(12) United States Patent
Brandle et al.

(10) Patent No.: US 7,927,851 B2
(45) Date of Patent: Apr. 19, 2011

(54) COMPOSITIONS HAVING ENT-KAURENOIC ACID 13-HYDROXYLASE ACTIVITY AND METHODS FOR PRODUCING SAME

(75) Inventors: Jim Brandle, London (CA); Alex Richman, London (CA)

(73) Assignee: Vineland Research and Innovation Centre, Ontario (CA)

( * ) Notice: Subject to any disclaimer, the term of this patent is extended or adjusted under 35 U.S.C. 154(b) by 0 days.

(21) Appl. No.: 11/725,574

(22) Filed: Mar. 19, 2007

(65) Prior Publication Data
US 2008/0064063 A1 Mar. 13, 2008

Related U.S. Application Data

(60) Provisional application No. 60/784,168, filed on Mar. 21, 2006.

(51) Int. Cl.
C12N 9/00 (2006.01)
C12N 9/02 (2006.01)
C12N 1/20 (2006.01)
C12N 15/00 (2006.01)
C07H 21/04 (2006.01)

(52) U.S. Cl. ......... 435/189; 435/183; 435/2; 435/252.3; 435/320.1; 536/23.2

(58) Field of Classification Search .................. None
See application file for complete search history.

(56) References Cited

FOREIGN PATENT DOCUMENTS
JP 3-277275 12/1991

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession A7NTM1, published Oct. 2, 2007.*
Brandle, J. E., et al., "Leaf ESTs from *Stevia rebaudiana*: A Resource for Gene Discovery in Diterpene Synthesis", *Plant Molecular Biology*, 50, (2002), 613-622.
Brandle, J. E., et al., "Steviol Glycoside Biosynthesis", *Phytochemistry*, 68, (2007), 1855-1863.
Geuns, J. M., "Molecules of Interest—Stevioside", *Phytochemistry*, 64, (2003),913-921.
Humphrey, T. V., et al., "Spatial Organisation of Four Enzymes from *Stevia rebaudiana* that are Involved in Steviol Glycoside Synthesis", *Plant Molecular Biology*, 61, (2006), 47-62.
Imler, S., et al., "Indole Alkaloid Biosynthesis in *Catharanthus roseaus*: New Enzyme Activities and Identification of Cytochrome P450 CYP72A1 as Secologanin Synthase", *The Plant Journal*, 24(6), (2000),797-804.
Jennewein, S., et al., "Taxol Biosythesis: Taxane 13α-Hydroxylase is a Cytochrome P450-Dependent Monooxygenase", *Proc. Natl. Acad. Sci. USA*, 98(24), (2001), 13595-13600.
Kim, K. K., et al., "Hydroxylation of *ent*-Kaurenoic Acid to Steviol in *Stevia rebaudiana* Bertoni—Purification and Partial Characterization of the Enzyme", *Archives of Biochemistry and Biophysics*, 332(2), (1996), 223-230.
Nelson, D. R., et al., "P450 Superfamily: Update on New Sequences, Gene Mappin, Accession Numbers and Nomenclature", *Pharmacogenetics*, 6, (1996),1-42.
Pompon, D., et al., "[6] Yeast Expression of Animal and Plant P450s in Optimized Redox Environments", *Methods of Enzymology*, 272, (1996),51-64.
Richman, A., et al., "Functional Genomics Uncovers Three Glucosyltransferases Involved in the Snythesis of the Major Sweet Glucosides of *Stevia rebaudiana*", *The Plant Journal*, 41, (2005),56-67.

* cited by examiner

*Primary Examiner* — Christian L Fronda
(74) *Attorney, Agent, or Firm* — Remenick PLLC

(57) ABSTRACT

The present invention relates to nucleotide sequences encoding ent-kaurenoic acid 13-hydroxylase polypeptides and polypeptides having ent-kaurenoic acid 13-hydroxylase activity. The invention also relates to methods of producing steviol and steviol glycosides.

5 Claims, 1 Drawing Sheet

US 7,927,851 B2

COMPOSITIONS HAVING ENT-KAURENOIC ACID 13-HYDROXYLASE ACTIVITY AND METHODS FOR PRODUCING SAME

RELATED APPLICATIONS

This application claims priority from U.S. Provisional Patent Application No. 60/784,168, filed on Mar. 21, 2006, which application is incorporated herein by reference.

FIELD OF INVENTION

The present invention relates to compositions and methods for producing sweeteners. More specifically, the present invention relates to compositions and methods for producing steviol and steviol glycosides.

BACKGROUND OF THE INVENTION

The worldwide demand for high potency sweeteners is increasing and, with blending of different sweeteners becoming a standard practice, the demand for alternatives is expected to increase. The sweet herb of Paraguay, Stevia rebaudiana Bertoni, produces an alternative high potency sweetener with the added advantage that Stevia sweeteners are natural plant products. In addition, the sweet steviol glycosides have functional and sensory properties superior to those of many high potency sweeteners. These glycosides accumulate in Stevia leaves where they may comprise from 10 to 20% of the leaf dry weight. Stevioside and rebaudioside A are both heat and pH stable (Chang and Cook, 1983), and suitable for use in carbonated beverages and many other foods. Stevioside is between 110 and 270 times sweeter than sucrose, rebaudioside A between 150 and 320 times sweeter than sucrose Early steps in steviol biosynthesis involve the plastid localized 1-deoxy-D-xylulose 5-phosphate (DXP) pathway, resulting in the formation of DXP from pyruvate and glyceraldehyde 3-phosphate by thiamine phosphate dependant DXP synthase (Totté et al. 2000), and leading ultimately to the synthesis of geranyl geranyl diphosphate (GGDP). Like all diterpenes, steviol is synthesized from GGDP, first by protonation-initiated cyclization to (−)-copalyl diphosphate (CDP) by CDP synthase (CPS) (Richman et al., 1999). Next, (−)-kaurene is produced from CDP by an ionization dependant cyclization catalysed by (−)-kaurene synthase (KS) (Richman et al., 1999). (−)-Kaurene is then oxidized at the C-19 position to (−)-kaurenoic acid, by a novel P450 mono-oxygenase. Steviol is produced by the hydroxylation of (−)-kaurenoic acid at the C-13 position, but the gene for this P450-dependant mono-oxygenase has not yet been isolated (Kim et al. 1996. Arch. Biochem. BioPhys. 332:223-230). Steviol glucosides are formed by four glycosylation reactions that start with steviol and end with rebaudioside A (Richman et al. 2005). The steps involve the addition of glucose to the C-13 hydroxyl, the transfer of glucose to the C-2' and C-3' of the 13-O-glucose and the addition of glucose to the hydroxyl of the C-4 carboxyl.

There is a need to identify methods of producing cells having the capability to synthesize steviol from ent-kaurenoic acid for use in synthesis of sweet steviol glycosides. However, the gene encoding ent-kaurenoic acid 13-hydroxylase is not known. There is a need in the art for compositions and methods for producing ent-kaurenoic acid 13-hydroxylase. There is also a need in the art for compositions and methods of producing steviol and steviol glycosides. Further, there is a need in the art for compositions and methods for producing steviol and steviol glycosides in cells, in plants and in vitro.

SUMMARY OF THE INVENTION

The present invention relates to compositions and methods for producing sweeteners. More specifically, the present invention relates to compositions and methods for producing steviol and steviol glycosides.

According to the present invention, there is provided a nucleotide sequence encoding an ent-kaurenoic acid 13-hydroxylase polypeptide defined by SEQ ID NO: 2.

Also according to the present invention, there is provided a nucleotide sequence comprising SEQ ID NO:1, a fragment or variant thereof. Wherein the fragment or variant thereof encodes a polypeptide exhibiting ent-kaurenoic acid 13-hydroxylase activity.

The present invention also provides a nucleotide sequence as defined above which hybridizes to SEQ ID NO:1 or its complement under stringent hybridization conditions. In a preferred embodiment, the stringent hybridization conditions comprise hybridization in 4×SSC at 65° C., for 8-16 hours, followed by washing in 0.1×SSC at 65° C. for an hour, or hybridization in 5×SSC and 50% formamide at 42° C. for 8-16 hours, followed by washing in about 0.5×SSC to about 0.2×SSC at 65° C. for about 1 hour. Wherein the nucleotide sequence encodes a polypeptide exhibiting ent-kaurenoic acid 13-hydroxylase activity.

Also contemplated by the present invention is a nucleotide sequence as defined above that exhibits between about 80% and 100% sequence identity with SEQ ID NO:1 and encodes a polypeptide exhibiting ent-kaurenoic acid 13-hydroxylase activity.

The present invention also provides a nucleotide construct comprising the nucleotide sequence as defined above. In an embodiment which is not meant to be limiting, the construct is an expression vector.

Also provided by the present invention is a polypeptide comprising an amino acid sequence defined by SEQ ID NO:2, or a biologically active fragment or variant thereof, the polypeptide exhibiting ent-kaurenoic acid 13-hydroxylase activity.

Further, the present invention contemplates a polypeptide as defined above wherein the polypeptide exhibits between about 52% to 100% sequence identity to SEQ ID NO:2, and exhibits ent-kaurenoic acid 13-hydroxylase activity.

Also contemplated by the present invention is a fusion protein of SEQ ID NO:2, a fragment or variant thereof that exhibits ent-kaurenoic acid 13-hydroxylase activity. In a preferred embodiment, which is not meant to be limiting in any manner, the fusion protein comprises SEQ ID NO:2 and a heterologous amino acid sequence selected from the group consisting of a membrane targeting sequence, an organelle targeting sequence, a secretion signal sequence, a purification sequence or any combination thereof.

The present invention further provides a cell comprising the nucleotide sequence or nucleotide construct as defined above. Without wishing to be limiting, the cell may be a plant cell, yeast cell, bacterial cell or mammalian cell. In a preferred embodiment, the cell is a plant cell.

Also provided by the present invention is a method of producing a polypeptide having ent-kaurenoic acid 13-hydroxylase activity in a cell comprising, a) transforming the cell with a nucleotide sequence encoding a polypeptide having ent-kaurenoic acid 13-hydroxylase activity, and;

b) translating the nucleotide sequence in the cell.

In a preferred embodiment, the cell is a plant cell. However, other cells may be employed to produce polypeptides having ent-kaurenoic acid 13-hydroxylase activity.

Also contemplated by the present invention is a method of producing steviol in a plant or plant cell comprising,
a) selecting a plant or plant cell that produces ent-kaurenoic acid;
b) transforming the plant or plant cell with a nucleotide sequence encoding a polypeptide having ent-kaurenoic acid 13-hydroxylase activity, and;
c) expressing the polypeptide having ent-kaurenoic acid 13-hydroxylase in the plant or plant cell to convert ent-kaurenoic acid to steviol.

The present invention also contemplates a method of producing a steviol glycoside in a plant or plant cell comprising,
a) selecting a plant or plant cell that produces ent-kaurenoic acid;
b) transforming the plant or plant cell with a first nucleotide sequence encoding a polypeptide having ent-kaurenoic acid 13-hydroxylase activity, and at least one other nucleotide sequence encoding one or more glucosyltransferases to catalyse the addition of one or more glucose molecules to steviol, or glucosyl-steviol;
c) expressing the polypeptide having ent-kaurenoic acid 13-hydroxylase and said one or more glucosyltransferases in the cell to convert ent-kaurenoic acid to one or more steviol glycosides.

Also contemplated is a method as defined above, wherein the steviol glycoside comprises stevioside, rebaudioside A, rebaudioside B, rebaudioside C, rebaudioside D, rebaudioside E, rebaudioside F, dulcoside, rubusoside, steviolmonoside, steviolbioside, 19-O-β glucopyranol-steviol or any combination thereof.

In an alternate embodiment, there is provided a method as defined above wherein the plant or plant cell is *Arabidopsis*, tobacco, sunflower, *Stevia rebaudiana*, *Thlapsi arvense* or a member of the Cruciferae family.

The present invention also provides an in-vitro method of producing steviol or one or more steviol glycosides comprising,
a) reacting ent-kaurenoic acid with a polypeptide having ent-kaurenoic acid 13-hydroxylase activity under conditions to produce steviol, and;
b) optionally reacting said steviol with one or more glucosyltransferases under conditions to produce one or more steviol glycosides.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
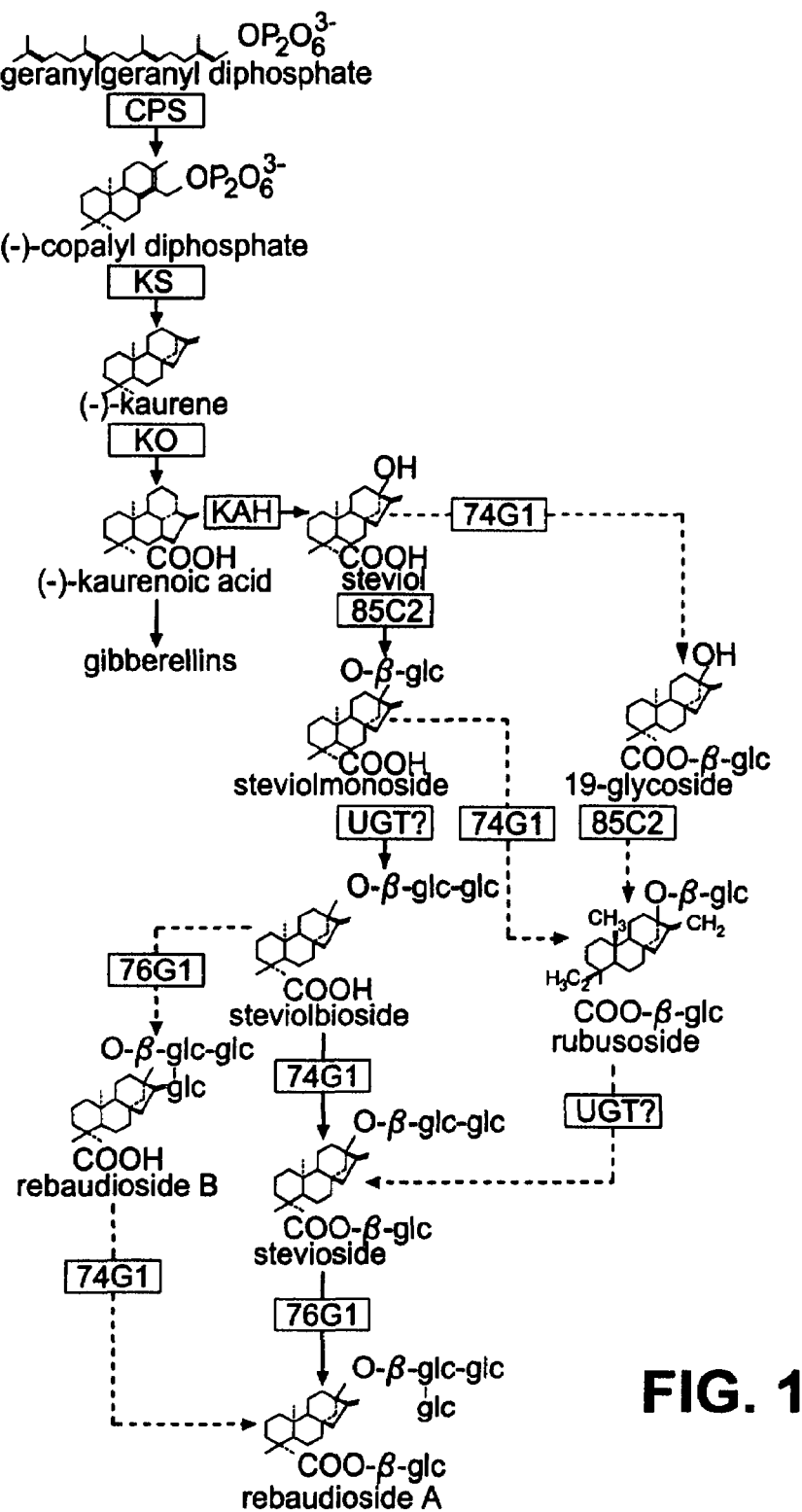
FIG. 1 shows a diagrammatic representation of biochemical pathways for the conversion of geranylgeranyl diphosphate to steviol and various steviol glycosides.

The present invention relates to compositions and methods for producing sweeteners. More specifically, the present invention relates to compositions and methods for producing steviol and steviol glycosides.

The following description is of a preferred embodiment.

According to an embodiment of the present invention, there is provided a nucleic acid encoding ent-kaurenoic acid hydroxylase that catalyses the conversion of ent-kaurenoic acid to steviol by mono-oxygenation (KAH, FIG. 1). In a further embodiment, there is provided a nucleotide sequence encoding an ent-kaurenoic acid 13-hydroxylase as defined by SEQ ID NO: 2, or a biologically active fragment or variant thereof. In a preferred embodiment, the nucleotide sequence encodes a polypeptide identical or substantially identical to the ent-kaurenoic acid 13-hydroxylase from *Stevia rebaudiana*.

By the term "steviol" it is meant the diterpenoic compound hydroxy-ent-kaur-16-en-13-ol-19-oic acid, which is the hydroxylated form of the compound termed "ent-kaurenoic acid", which is ent-kaur-16-en-19-oic acid (see FIG. 1).

By the term "steviol glycoside" it is meant any of the glycosides of the aglycone steviol including, but not limited to stevioside, rebaudioside A, rebaudioside B, rebaudioside C, rebaudioside D, rebaudisode E, rebaudisode F, dulcoside, rubusoside, steviolmonoside, steviolbioside, and 19-O-β glucopyranosol-steviol.

By ent-kaurenoic acid 13-hydroxylase activity it is meant the activity associated with a polypeptide, either a full length or a fragment, that is capable of catalyzing or partially catalyzing the conversion of ent-kaurenoic acid to steviol by mono-oxygenation. Preferably, the polypeptide is ent-kaurenoic acid 13-hydroxylase, or a fragment thereof that is capable of catalyzing or partially catalyzing the conversion of ent-kaurenoic acid to steviol by mono-oxygenation.

By "operatively linked" it is meant that the particular sequences interact either directly or indirectly to carry out an intended function, such as mediation or modulation of gene expression. The interaction of operatively linked sequences may, for example, be mediated by proteins that interact with the operatively linked sequences.

The present invention contemplates a nucleotide sequence encoding an ent-kaurenoic acid 13-hydroxylase or a biologically active fragment or variant thereof, provided that the fragment or variant encodes a polypeptide exhibiting ent-kaurenoic acid 13-hydroxylase activity. In a preferred embodiment, the nucleotide sequence comprises SEQ ID NO:1. However, the nucleotide sequence may also include variants that comprise between about 80% to 100% sequence similarity, or any amount therebetween with SEQ ID NO:1, for example, but not limited to about 80%, 82%, 85%, 87%, 90%, 91%, 92%, 93%, 94%, 95%, 96%, 97%, 98%, 99% or about 100% homology, or any amount therebetween. To determine whether a nucleic acid exhibits similarity with the sequences presented herein, oligonucleotide alignment algorithms may be used, for example, but not limited to a BLAST (GenBank, see: ncbi.nlm.nih.gov/cgi-bin/BLAST/, using default parameters: Program: blastn; Database: nr; Expect 10; filter: default; Alignment: pairwise; Query genetic Codes: Standard (1)), BLAST2 (EMBL see: embl-heidelberg.de/Services/index.html, using default parameters: Matrix BLOSUM62; Filter: default, echofilter: on, Expect: 10, cutoff: default; Strand: both; Descriptions: 50, Alignments: 50), or FASTA, search, using default parameters. Similar algorithms may be employed to determine sequence identity between two or more amino acid sequences.

When compared to known cytochrome P450 enzymes ent-kaurenoic acid 13-hydroxylase, as defined by SEQ ID NO: 2, shows the highest sequence identity (51% identity) to CYP72A1, a *Catharanthus roseus* cytochrome P450-dependant monoxygenase known as secologanin synthase that catalyses oxidative ring cleavage in the synthesis of the terpene indole alkaloid secologanin (Irmler et al. 2000. Plant J. 24:797-804). *Catharanthus* does not produce steviol. In the current nomenclature system P450 enzymes that share 40% identity at the amino acid level are in the same family, those that share at least 55% amino acid are in the same subfamily (Nelson et al. 1996. Pharmacogenetics 6:1-42). Since ent-kaurenoic acid 13-hydroxylase has greater than 40% identity with CYP72A1 they may both be members of the family of CYP72 P450 enzymes. Ent-kaurenoic acid 13-hydroxylase is less than 55% identical to CYP72A1 and does not share greater than 55% with any other member of the CYP72A subfamily, suggesting that it is not part of the CYP72A subfamily.

Therefore, according to an alternate embodiment of the present invention, there is provided a polypeptide comprising an amino acid sequence defined by SEQ ID NO:2 or a biologically active fragment or variant thereof, the polypeptide exhibiting ent-kaurenoic acid 13-hydroxylase activity. In a preferred embodiment, the polypeptide comprises about 52% to 100% sequence identity, or any amount therebetween, with SEQ ID NO: 2, for example, 52%, 55%, 60%, 65%, 70%, 75%, 80%, 85%, 90%, 95%, 96%, 97%, 98%, 99%, 99.5%, 99.9% or 100% identity, and exhibits ent-kaurenoic acid 13-hydroxylase activity.

Also encompassed by the present invention are polypeptides comprising a fusion protein of SEQ ID NO: 2, or a biologically active fragment or variant thereof and a heterologous amino acid sequence for example, but not limited to a membrane targeting sequence, an organelle targeting sequence, a secretion signal, an amino acid sequence that facilitates purification of the fusion protein, or a combination thereof. In an embodiment, which is not meant to be limiting in any manner, the heterologous amino acid sequence may comprise a P450 reductase, for example, but not limited to a P450 reductase from *Stevia* or *Arabidopsis*.

The present invention also contemplates any nucleotide sequence encoding the polypeptide of SEQ ID NO:2, and any nucleotide sequence encoding a fusion protein comprising SEQ ID NO:2.

The present invention also includes nucleotide sequences encoding polypeptides having ent-kaurenoic 13-hydroxylase activity and that hybridize to SEQ ID NO:1 under stringent hybridization conditions (see Maniatis et al., in Molecular Cloning (A Laboratory Manual), Cold Spring Harbor Laboratory (1982) p 387 to 389; Ausubel, et al. (eds), 1989, *Current Protocols in Molecular Biology*, Vol. 1, Green Publishing Associates, Inc., and John Wiley & Sons, Inc., New York, at p. 2.10.3)). Without wishing to be limiting in any manner, representative examples of such stringent hybridization conditions include hybridization in 4×SSC at 65° C. for 8-16 hours, or any time therebetween, followed by washing in 0.1×SSC at 65° C. for an hour or hybridization in 5×SSC and 50% formamide at 42° C. for 8-16 hours or any time therebetween, followed by washing in about 0.5×SSC to about 0.2×SSC at 65° C. for one hour. However, hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH.

The nucleotide sequence of the present invention preferably encodes a polypeptide that exhibits ent-kaurenoic acid 13-hydroxylase activity. In a preferred embodiment, the polypeptide exhibits about the same activity as the polypeptide defined by SEQ ID NO:2 when tested under substantially identical conditions. However, it is also contemplated that the polypeptide may exhibit more or less activity than SEQ ID NO:2 for example, but not limited to about 50%, 60%, 70%, 80%, 90%, 100%, 110%, 120%, 150% or more when tested under substantially identical conditions. Preferably, the activity is greater than about 50%, 60%, 70%, 80%, 90%, or more. It is also contemplated that the ent-kaurenoic acid 13-hydroxylase activity of the polypeptide may be defined by an amount between the range of any two of the values listed above.

A variety of methods and assays may be employed to measure the conversion of ent-kaurenoic acid to steviol, for example, but not limited to one or more chromatographic techniques including, but not limited to high performance liquid chromatography (HPLC), thin layer chromatography (TLC), and the like, mass spectroscopy including, but not limited to electrospray ionization (ESI), collision induced dissociation (CID) and the like or any combination thereof, for example, but not limited to liquid chromatography-electrospray mass spectroscopy (LC-ES/MS). A representative example of an assay for ent-kaurenoic acid 13-hydroxylase activity, which is not meant to be limiting is described in Example 7.

It is also contemplated that the nucleotide sequence of the present invention may comprise part of a larger nucleic acid sequence or nucleotide construct, for example, but not limited to a recombinant expression vector, plasmid, artificial chromosome or the like. Such a nucleotide construct may comprise a variety of sequences including, but not limited to selectable marker genes, one or more origins of replication, multi-cloning or restriction endonuclease sites, and regulatory sequences including, without limitation one or more promoters, enhancers or a combination thereof.

A regulatory sequence may also include, but is not limited to promoter elements, basal (core) promoter elements, elements that are inducible in response to an external stimulus, elements that mediate promoter activity such as negative regulatory sequences or transcriptional enhancers. Regulatory sequences may also comprise elements that are active following transcription, for example, regulatory sequences that modulate gene expression such as translational and transcriptional enhancers, translational and transcriptional repressors, upstream activating sequences, and mRNA instability determinants. Several of these latter elements may be located proximal to the coding region. In the context of this disclosure, the regulatory sequence typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory sequence that provides for the recognition for RNA polymerase or other transcriptional factors to ensure initiation at a particular site is a promoter sequence. A promoter sequence comprises a basal promoter sequence, responsible for the initiation of transcription, as well as other regulatory sequences (as listed above) that modify gene expression.

There are also several types of regulatory sequences, including those that are developmentally regulated, inducible and constitutive. A regulatory sequence that is developmentally regulated, or controls the differential expression of a gene under its control, is activated within certain organs or tissues of an organ at specific times during the development of that organ or tissue. However, some regulatory sequences that are developmentally regulated may preferentially be active within certain organs or tissues at specific developmental stages, they may also be active in a developmentally regulated manner, or at a basal level in other organs or tissues within the organism as well.

An inducible regulatory sequence is one that is capable of directly or indirectly activating transcription of one or more DNA sequences or genes in response to an inducer. In the absence of an inducer the DNA sequences or genes will not be transcribed. Typically the protein factor, that binds specifically to an inducible sequence to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. In respect of a plant or plant cell and without wishing to be bound by theory or limiting in any manner, a plant cell containing an inducible sequence may be exposed to an inducer by externally applying the inducer to the cell or plant such as by spraying, watering, heating or similar methods. Inducible elements may be derived from either plant or non-plant genes (e.g. Gatz, C. and Lenk, I. R. P., 1998, Trends Plant Sci. 3, 352-358). Examples, of potential inducible promoters include, but are not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180), cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A plant constitutive sequence directs the expression of a gene throughout the various parts of a plant and continuously throughout plant development. Examples of known constitutive sequences include promoters associated with the CaMV 35S transcript (Odell et al., 1985, Nature, 313: 810-812), the rice actin 1 (Zhang et al, 1991, Plant Cell, 3: 1155-1165) and triosephosphate isomerase 1 (Xu et al, 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive sequence is expressed at the same level in all cell types, but that the gene is expressed in a wide range of cell types even though variation in abundance is often observed.

The nucleotide sequences or constructs of the present invention may be introduced into cells using any suitable transformation system known in the art. For example, but not wishing to be limiting, the nucleotide constructs of the present invention can be introduced into plant cells using Ti plasmids, Ri plasmids, plant virus vectors, direct DNA transformation, micro-injection, electroporation, etc. A further method for the introduction of nucleotide sequences or constructs into a plant cell is to dip developing floral tissues into a solution containing *Agrobacterium tumefaciens* harbouring the nucleotide construct, sucrose and a surfactant (Clough and Bent. 1998. Plant J. 16:735-743). In addition to the methods described above, several methods are known in the art for transferring DNA vectors into plant species, including gymnosperms, angiosperms, monocots and dicots (e.g. Newell. 2000. Mol. Biotech. 16:53-65). Representative examples include DNA uptake by protoplasts, polyethylene glycol mediated uptake by protoplasts, and bombardment of cells with DNA laden microprojectiles (Plant Gene Transfer and Expression Protocols. Humana Press, Totowa, N.J.). Minor modifications to these protocols make them applicable to a broad range of plant species. For reviews of several techniques see for example Weissbach and Weissbach, Methods for Plant Molecular Biology, Academy Press, New York VIII, pp. 421-463 (1988); Geierson and Corey, Plant Molecular Biology, 2d Ed. (1988); and Miki and Iyer, Fundamentals of Gene Transfer in Plants. In Plant Metabolism, 2d Ed. D T. Dennis, D H Turpin, D D Lefebrve, D B Layzell (eds), Addison Wesly, Langmans Ltd. London, pp. 561-579 (1997).

Without wishing to be limiting, plant cells that comprise a nucleotide sequence of the present invention may be selected for by one or more selection steps. By the term "selecting" it is meant identifying plant cells, tissues or plants which comprise the nucleotide sequence of the present invention from similar plant cells, tissues or plants which lack the nucleotide sequence. Selecting may involve, but is not limited to altering the growth or development of plant cells, tissue or plants which lack the nucleotide sequence in a manner which permits such cells, tissue or plants to be differentiated or identified from plants expressing the nucleotide sequence of the present invention. Further, selecting may involve killing plant cells, tissue or plants that lack the nucleotide sequence. Alternatively, selecting may involve Southern hybridization to identify plant cells comprising the nucleotide sequence, Northern hybridization to identify plant cells comprising and expressing the nucleotide sequence, or Western analysis to identify plants cells comprising and expressing a protein, or fragment of the protein of interest, for example, an ent-kaurenoic acid 13-hydroxylase. Further, selecting may involve an enzymatic assay to measure conversion of ent-kaurenoic acid to steviol. Other selection strategies are also possible and are fully contemplated by the method of the present invention.

The nucleotide sequences of the present invention may be expressed in a variety of cells including, but not limited to yeast, bacteria, plants, insect and mammalian cells. Thus, the cells or organisms comprising the cells may serve as an expression system for the production of ent-kaurenoic acid 13-hydroxylase. Accordingly, the present invention contemplates a cell transformed with a nucleotide sequence encoding ent-kaurenoic acid 13-hydroxylase. In a preferred embodiment, a plant cell is transformed and expresses ent-kaurenoic acid 13-hydroxylase. In an alternate embodiment, a seed, plant or plant tissue, for example, but not limited to leaves, stem, petals or the like is transformed and expresses the nucleotide sequence of the present invention.

Cell cultures derived from multicellular organisms and multicellular organisms, such as plants, may be used as hosts to practice the invention. Plants such as tobacco and *Arabidopsis*, members of the Cruciferae family, for example, but not limited to *Thalapsi arvense*, members of the genus *Stevia*, for example, but not limited to *Stevia rebaudiana*, or other plants such as, but not limited to sunflower that are enriched in ent-kaurenoic acid are preferred.

As an example that is not meant to be limiting in any manner, the DNA encoding ent-kaurenoic acid 13-hydroxylase can be placed under the control of the 35S enhancer-promoter plus AMV leader sequence, which may optimize transcription and translation (Kay et al. 1987. Science 236: 1299-1301; Jobling and Gehrke. 1987. Nature 325:622-625). Other promoters such as the tCUP constitutive promoter system from tobacco can also be used to direct expression (Foster et al. 1999. Plant Mol. Biol. 41:45-55). The nos terminator may be used to ensure stability of the resulting RNA and to terminate transcription. The completed expression vector may be cloned into a binary plasmid containing the T-DNA border sequences. This plasmid can then be transformed into *Agrobacterium tumefaciens*, and into a plant genome using *Agrobacterium* mediated transformation (Horsch et al. 1985. Science 227:1229-1231). The plant selectable marker can be an antibiotic such as gentamycin, hygromycin, kanamycin, and the like. Similarly, enzymes providing for production of a compound identifiable by colour change such as GUS (beta-glucuronidase), or luminescence, such as luciferase neomycin phosphotransferase may also be used. Transformed plantlets may be selected through the selectable marker by growing the transformed cells on a medium containing the selection agent (e.g. kanamycin) and appropriate amounts of phytohormones such as naphthalene acetic acid and benzyladenine for callus and shoot induction. The plant cells may then be regenerated and the resulting plants transferred to soil using techniques well known to those skilled in the art.

Although, expression of ent-kaurenoic acid hydroxylase is preferred in plants, expression of the nucleotide sequence in other non-plant cells, for example yeast or bacteria is also contemplated. As a representative example, which is not meant to be limiting in any manner, prokaryotic organisms such as bacteria can be used to practice this invention. The DNA, or cDNA may be modified to increase translation of the mRNA encoding the polypeptide of the present invention in the desired host organism. For example, methods known in the art can be used to introduce a NcoI site at the terminus of the nucleotide sequence. A membrane anchor functional in bacteria may also be introduced.

In embodiments wherein ent-kaurenoic acid hydroxylase is expressed in bacteria, a suitable P450 reductase may also be coexpressed. Further, a fusion can be created between ent-kaurenoic acid 13-hydroxylase and suitable P450 reductase, for example, but not limited to, a *Stevia rebaudiana* P450 reductase (Irmler et al. 2000. Plant J. 24:797-804). The fusion protein can be expressed in suitable host cells such as *E. coli*, for example, but not limited to BL21, BL21(DE3), or BL21 (DE3)pLysS, however other strains of *E. coli* and many other species or genera of prokaryotes may be used. As a representative example, cDNA sequences of ent-kaurenoic acid 13-hydroxylase may be transferred to expression vectors such as the commercially available pET30a, b or c (Novagen). The ent-kaurenoic acid 13-hydroxylase-P450 reductase fusion may be ligated into the pET30a plasmid. In this case, the ent-kaurenoic acid 13-hydroxylase-P450 reductase fusion would be under the control of the T7 polymerase promoter. Following induction of expression with IPTG the ent-kaurenoic acid 13-hydroxylase-P450 reductase protein may be produced, and potentially comprise up to about 50% of the total cell protein. The membrane fraction of the cells could then be isolated or whole cells lysed and used in enzyme assays, for example, for the synthesis of steviol.

As a further representative example, which is not meant to be limiting in any manner, eukaryotic microbes such as yeasts also may be used to practice this invention, including but not limited to *Saccharomyces cerevisiae*, although other strains and species may be used. The plasmid pYEDP60 is commonly used as an expression vector in yeast (Pompon et al. 1996. Methods Enzymol. 272:51-64). This plasmid contains the URA3 marker that provides a selection for a mutant strain of yeast that cannot grow without uracil, such as strains WAT11U and WAT21U (Urban et al. 1997. J. Biol. Chem. 272:19176-19186). The presence of the ura3 mutation in the yeast host cell genome provides an effective environment for detecting transformation by growth in the absence of uracil. The yeast strain WAT11 whose microsomal P450 reductase allele has been mutated and replaced with the *Arabidopsis thaliana* P450 reductase isoform 1 is a suitable for use with the pYEDP60 plasmid. When grown on media containing galactose the WAT11 yeast strain can over produce *Arabidopsis* P450 reductase isoform 1. Other strains of yeast such as WAT21 whose microsomal P450 reductase allele has been mutated and replaced with the *Arabidopsis thaliana* P450 reductase isoform 2 are also suitable for use with the pYEDP60 plasmid.

It is also contemplated that ent-kaurenoic acid 13-hydroxylase-P450 reductase fusions may be expressed using the pYES/NT plasmid and a yeast strain such as, but not limited to INVSc. Following induction of expression, the membrane fraction of the cells may be isolated or whole cells lysed and used in enzyme assays, for example, for the synthesis of steviol.

As will be apparent to those skilled in the art, other yeast strains and expression vectors can be used to produce polypeptides having ent-kaurenoic acid 13-hydroxylase activity. Yeast expression vectors usually have a bacterial origin of replication, a yeast origin of replication, selectable marker genes for selection of transformed cells, one or more yeast expression promoters, and a multi-cloning site for insertion of heterologous DNA sequences. Examples of other expression vectors include, but are not limited to, pESC (Stratagene), and yeast strains like G1315.

The present invention also contemplates nucleotide sequences that comprise at least 15 consecutive nucleotides of SEQ ID NO:1, for example at least 15, 17, 20, 21, 25, 30, 35, 40, 45, 50, 55, 60, 70, 75, 100, 150, 200, 250, 300, 350, 400, 500, 600, 700, 800, 900, 1000, 1100, 1200, 1300, 1400, 1500 or more consecutive nucleotides of SEQ ID NO:1. In a preferred embodiment, the nucleotide sequence is labeled with a marker, for example, but not limited to a fluorescent group or radioactive label that facilitates identification of the nucleotide sequence. In such a manner, the nucleotide sequence may be employed as a probe to detect similar or identical sequences, for example, in cells, organisms, assays or any combination thereof.

The nucleotide sequences described above also may be used as primers, for example, in PCR amplification reactions or the like. For example, the nucleotide sequences may be employed to obtain homologs of the ent-kaurenoic acid 13-hydroxylase gene of *Stevia rebaudiana* from other organisms. Without wishing to be limiting, this may be accomplished by contacting the DNA of a steviol-producing organism with primers under stringent hybridization conditions to permit the primers to hybridize to a ent-kaurenoic acid 13-hydroxylase gene of the organism. This may be followed by amplifying, isolating and optionally characterizing the ent-kaurenoic acid 13-hydroxylase gene from the organism.

The present invention is also directed to an antisense, short-interfering or RNAi nucleotide sequences with sufficient complementarity to at least a continuous portion of SEQ ID NO:1 to enable hybridization therewith. Preferably, such a nucleotide sequence comprises a complementary sequence of at least 15 consecutive nucleotides of SEQ ID NO:1, for example at least 15, 17, 20, 21, 25, 30, 35, 40, 45, 50, 55, 60, 70, 75, 100, 150, 200, 250, 300, 350, 400, 500, 600, 700, 800, 900, 1000, 1100, 1200, 1300, 1400, 1500 or more consecutive nucleotides. The antisense, short interfering or RNAi nucleotide sequence may be employed to downregulate, or otherwise reduce gene expression of ent-kaurenoic acid 13-hydroxylase activity.

By reducing gene expression, it is meant the reduction in the level of mRNA, protein, or both mRNA and protein, encoded by a gene or nucleotide sequence of interest. Reduction of gene expression may arise as a result of the lack of production of full length RNA, for example mRNA, or through cleaving the mRNA, for example with a ribozyme (e.g. see Methods in Molecular Biology, vol 74 *Ribozyme Protocols*, P. C. Turner, ed, 1997, Humana Press), or RNAi (e.g. see *Gene Silencing by RNA Interference, Technology and Application*, M. Sohail ed, 2005, CRC Press), or otherwise reducing the half-life of RNA, using antisense (e.g. see *Antisense Technology, A Practical Approach*, C. Lichtenstien and W. Nellen eds., 1997, Oxford University Press), ribozyme, or RNAi techniques.

The nucleotide sequences of the present invention may be used in the production, isolation, purification, downregulation or any combination thereof of ent-kaurenoic acid 13-hydroxylase. Further, the nucleotide sequences and polypeptides of the present invention may be used in the production, isolation, purification or any combination thereof of steviol, the primary enzyme product of ent-kaurenoic acid 13-hydroxylase, or steviol glycosides such as, but not limited to stevioside, rebaudioside A, rebaudioside B, rebaudioside C, rebaudioside D, rebaudioside E, rebaudioside F, dulcoside, rubusoside, steviolmonoside, steviolbioside, 19-O-β glucopyranosol-steviol, or any combination thereof.

Metabolic pathways for the production of steviol and the conversion of steviol to various steviol glycosides are shown in FIG. 1 and further described in Brandle et al., (2002) Plant Molecular Biology 50: 613-622; Richman et al., (1999) The Plant Journal 19(4), 411-421; Richman et al., (2005) The Plant Journal 41, 55-67, which are herein incorporated by reference).

In an alternate embodiment of the present invention, there is provided a method of producing steviol in a host, for example but not limited to a plant cell, that endogenously produces ent-kaurenoic acid comprising transforming the host or plant cell with a nucleotide sequence encoding ent-kaurenoic acid 13-hydroxylase, and expressing ent-kaurenoic acid 13-hydroxylase in the cell. In this manner ent-kaurenoic acid 13-hydroxylase can convert kaurenoic acid present in the cell to steviol. The steviol so produced may then be extracted from the host. In a preferred embodiment, the host is a plant or a plant cell from tobacco, *Arabidopis*, or members of the Cruciferae family, for example, but not limited to *Thalapsi arvense*, members of the genus *Stevia*, for example, but not limited to *Stevia rebaudiana*, or other plants such as, but not limited to sunflower that are enriched in ent-kaurenoic acid are preferred.

In an alternate embodiment of the present invention, there is provided a method of producing steviol in a host, for example but not limited to a plant cell, that endogenously produces ent-kaurenoic acid. In this method, a host or plant cell is provided that comprises a nucleotide sequence encoding ent-kaurenoic acid 13-hydroxylase. The nucleotide sequence is expressed in the cell, so that the ent-kaurenoic acid 13-hydroxylase converts any kaurenoic acid present in the cell to steviol.

It is also contemplated that steviol can be produced in a host, for example but not limited to, a plant or plant cell, that does not naturally produce ent-kaurenoic acid hydroxylase. Accordingly, there is provided a method of producing steviol in a host or plant cell comprising transforming the host, plant or plant cell with one or more nucleotide sequences encoding one or more enzymes that produce ent-kaurenoic acid, expressing the one or more enzymes in the host, plant or plant cell, re-transforming the host, plant or plant cell with a nucleotide sequence encoding ent-kaurenoic acid 13-hydroxylase, and expressing ent-kaurenoic acid hydroxylase in the host, plant or plant cell. In this manner one or more enzymes within the host, plant or plant cell may act on one or more substrates to produce ent-kaurenoic acid and subsequently ent-kaurenoic acid hydroxylase can convert the ent-kaurenoic acid to steviol.

Steviol can also be produced in a host, for example but not limited to a plant or plant cell that does not naturally produce ent-kaurenoic acid hydroxylase, by providing a host, plant or plant cell that comprises one or more nucleotide sequences encoding one or more enzymes that produce ent-kaurenoic acid, and a second nucleotide sequence that encodes ent-kaurenoic acid 13-hydroxylase, and co-expressing the one or more nucleotide sequences, and the second nucleotide sequence in the host, plant or plant cell. The one or more nucleotide sequences and the second nucleotide sequence may be introduced into the host via transformation, or one host comprising the one or more nucleotide sequences, may be crossed with a second host comprising the second nucleotide sequence.

In a further embodiment, there is also contemplated downregulating the activity of ent-kaurenoic acid oxidase in a host cell, plant or enzyme system where the down regulation of oxidase activity increases the availability of kaurenoic acid for conversion to steviol through the reaction mediated by ent-kaurenoic acid 13-hydroxylase. The ent-kaurenoic acid oxidase activity may be downregulated by any suitable method known in the art, for example, but not limited to antisense, RNAi, or short-interfering RNA technology, production of dominant negatives or molecular decoys, gene knockout, and the like.

Therefore, the present invention also provides a method for steviol biosynthesis that involves providing a host, plant or plant cell that comprises a first nucleotide sequence encoding a sequence that down-regulates ent-kaurenoic acid oxidase expression, and a second nucleotide sequence that encodes ent-kaurenoic acid 13-hydroxylase, and co-expressing the first and second nucleotide sequences in the host, plant or plant cell. The first and the second nucleotide sequences may be introduced into the host via transformation, or by crossing one host comprising the first nucleotide sequence, with a second host comprising the second nucleotide sequence.

In a further embodiment, there is provided a method of producing one or more steviol glycosides in a plant or plant cell comprising,
  a) selecting a plant or plant cell that produces ent-kaurenoic acid;
  b) transforming the plant or plant cell with a first nucleotide sequence encoding a polypeptide having ent-kaurenoic acid 13-hydroxylase activity, and at least one second nucleotide sequence encoding one or more glucosyltransferases to catalyze the addition of one or more glucose molecules to steviol or a glucosylated steviol substrate, and;
  c) expressing the polypeptide having ent-kaurenoic acid 13-hydroxylase activity and said one or more glucosyltransferases in the cell to convert ent-kaurenoic acid to one or more steviol glycosides.

The first and the second nucleotide sequences may be introduced into the host via transformation, or by crossing one host comprising the first nucleotide sequence, with a second host comprising the second nucleotide sequence.

In an embodiment of the present invention, which is not meant to be considered limiting in any manner, the one or more glucosyltransferases may comprise any glucosyltranferase or combination of glucosyltranferases known in the art, for example, but not limited to UGT76G1, UGT85C2, UGT74G1 (Richman et al. 2005. Plant J. 41:56-67, which is incorporated herein by reference), any of the glucosyltranferases described in JP 3-277275 (which is incorporated herein by reference), or any combination thereof.

It is known that plants such as, but not limited to *Arabidopsis* and tobacco have the inherent ability to glucosylate steviol at the C-19 position of the C-4 carboxyl, due to native glucosyltranferase activity. Introduction of kaurenoic acid 13-hydroxylase into a host cell or plant such as, but not limited to tobacco or *Arabidopsis* results in the synthesis of steviol from the ubiquitous substrate kaurenoic acid, and as a result of endogenous glucosyltranferase activity, may result in the production of 19-O-β glucopyranosol-steviol. Subsequent introduction of the glucosyltransferase, UGT85C2 (Richman et al. 2004. Plant J. 41:56-67), into the host cell can catalyze the addition of glucose to the C-13 hydroxyl of 19-O-β glucopyranosol-steviol resulting in the production of 13,19-O-β glucopyranosol-steviol, also know as rubusoside.

In the absence of a native enzyme in the host cell that is able to glucosylate steviol at the C-19 position of the C-4 carboxyl, a gene coding for the glucosyltransferase enzyme, for example, but not limited to UGT74G1 from *Stevia*, can be introduced to allow the synthesis of sweet steviol glycosides from kaurenoic acid. In sunflower, rubusoside could be synthesized by introducing kaurenoic acid 13-hydroxylase to allow steviol synthesis, UGT85C2 to allow steviolmonoside synthesis and UGT74G1 to allow rubusoside synthesis. Any glucosyltransferase known in the art that can glucosylate steviol resulting in any steviol glycoside may be employed herein. Examples of additional enzymes that may be employed to produce steviol glycosides are provided in JP 3-277275, which is herein incorporated by reference in its entirety.

The present invention will be further illustrated in the following examples.

EXAMPLES

Example 1

Plant Material and the Generation of Expressed Sequence Tags

Actively growing *S. rebaudiana* leaves (approximately 4.5 cm in length) were harvested from field plots grown at Delhi, Canada then immediately frozen in liquid nitrogen. Messenger RNA was isolated and a lambda ZAP Express cDNA library was constructed as described previously (Richman, A. S., Gijzen, M., Starratt, A. N., Yang, Z. and Brandle, J. E. 1999. Plant J 19:(4) 411-421). Phagemid clones in *E. coli* were obtained using the mass excision protocol as outlined in the ZAP Express cDNA synthesis kit (Stratagene, La Jolla, Calif.).

Phagemid DNA was prepared by inoculating 96-well deep-well blocks filled with 1.2 mL LB (supplemented with kanamycin at 50 µg/mL) with randomly picked bacterial colonies. Blocks were incubated for 22 h at 37° C. and 600 rpm in a Stratagene Tempest thermoshaker. Phagemid DNA was purified using Qiaprep 96 Turbo miniprep kits (Qiagen, Mississauga, Ontario, Canada) and a Biomek2000 automated laboratory workstation (Beckman Coulter, Fullerton, Calif.). Sequencing of the 5' ends of the cDNA clones (via a T3 promoter primer) was conducted with the ABI PRISM Big Dye terminator DNA sequencing kit (Applied Biosystems, Foster City, Calif.) and an ABI 377 DNA sequencer (Applied Biosystems).

To facilitate the analysis and annotation processes, ESTs were edited to remove contaminating or poor quality data. Vector sequences were identified and removed from the ESTs using TIGR's "LUCY" algorithm (see: tigr.org/softlab/). Poor quality ends were automatically trimmed by a locally produced algorithm that continuously removed terminal bases until less than three ambiguous ('N') base calls were present in a 50 base pair window. PolyA (T) tails, if present, were removed manually. Foreign genomic and bacterial sequences were identified by BLASTN comparisons against REPBASE, and the nucleotide database of *E. coli*. (Jurka, J. 2000. Trends Genet 16:(9) 418-420; Blattner, F. R., Plunkett, G. III, Bloch, C. A., Perna, N. T., Burland, V., Riley, M., Collado-Vides. J., Glasner, J. D., Rode, C. K., Mayhew, G. F., Gregor, J., Davis, N. W., Kirkpatrick, H. A., Goeden, M. A., Rose, D. J., Mau, B. and Shao, Y. 1997. Science 277: 1453-1474.). ESTs were also searched against the *Arabidopsis* chloroplast and *Arabidopsis* mitochondrial nucleotide databases (Sato, S., Nakamura, Y., Kaneko, T., Asamizu, E. and Tabata, S. 1999. Complete structure of the chloroplast genome of *Arabidopsis thaliana*. DNA Res 6:(5) 283-290; Unseld, M., Marienfeld, J. R., Brandt, P. and Brennicke, A. 1997. Nature Genet 15: (1) 57-61). The complete set of ESTs were assigned accession numbers BG521336 to BG526883.

The functional assignment of ESTs was based on the results of a comparison to the non-redundant (nr) protein database of GenBank, using the BLASTX algorithm, and default settings (Altschul, S. F., Madden, T. L., Schäffer, A. A., Zhang, J., Zhang, Z., Miller, W. and Lipman, D. J. 1997. Nucleic Acids Res 25:3389-3402). A significant similarity was declared when the score was greater than 100 and $e<10^{-14}$, ESTs with scores of between 1 and 99 were assigned to the "novel" category, while those with no similarities were assigned to "no hits". ESTs were assigned to putative cellular roles using the categories developed by Bevan et al. (Bevan, M., Bancroft, I., Bent, E., Love, K., Goodman, H. and Dean, C., et al. 1998. Nature 391: 485-488). Where appropriate, multi-functional genes were assigned to multiple cellular roles. The process was assisted by examination of published cellular roles of similar genes found within the NCBI's Entrez and PUBMED directories, TIGR *Arabidopsis thaliana* annotation database (see: tigr.org/tdb/index.shtml), the MIPS *Arabidopsis* database (see: mips.biochem.mpg.de/proj/thal), and the Yeast Genome Directory (Mewes, H. W., Albermann, K., Bähr, Frishman, D., Gleissner, A., Hani, J., Heumann, K., Kleine, K., Maieri, A., Oliver, S. G., Pfeiffer, F. and Zollner, A. 1997. Nature 387:7-65). Assignment of ESTs to cellular roles was accelerated by assembly of ESTs into clusters using the SeqMan II module of DNAStar (DNAStar Inc. Madison, Wis.).

Consensus sequences of all ESTs were generated using a 90% homology over a minimum of 15 base pairs. Low matching ESTs forming contigs with previously annotated ESTs, and manually verified as accurate sequence overlaps, received the same name and cellular role category. A locally developed relational database management system (EST Commander), using the aforementioned data sources, was used to manually assign individual ESTs to cellular roles.

Example 2

Identification of Ent-Kaurenoic Acid 13-hydroxylase Candidates

Candidate ESTs were identified using a keyword search of the annotated EST database and the keywords "P450" and "CYP". Seventy-four ESTs matching the "P450" keyword criteria were identified. The BLAST search from each of the ESTs was examined and candidates were identified with similarity to cytochrome P450-dependant monooxygenases involved in the hydroxylation of polycyclic molecules. Twenty-eight of those ESTs were orthologs of ent-kaurene oxidase. Entries with high levels of similarity to genes of known functions that are not similar to the hydroxylation of ent-kaurenoic acid or are identical to SrKO1 or SrKO2 were eliminated. Of the candidate ESTs, 13 were identified (belonging to 6 different genes). ESTs were deemed representative of the same gene by comparing the region of overlap between the single pass sequencing runs. ESTs that were about 90% identical with each other were considered to represent the same gene. Mismatches are due to poor quality base calls.

Gene 1 is represented by 3 ESTs (8-40; GenBank Accession No. BG524863, SEQ ID No. 3, 24-31; GenBank Accession No. BG522690, SEQ ID No. 4; 79-54 SEQ ID No. 5) and has similarity to a cytochrome P450-dependant monooxygenase (CYP72A1, secologanin synthase from *Catharanthus roseus*, Genbank Accession No. AAA33106) that catalyses oxidative ring cleavage in the synthesis of the terpene indole alkaloid secologanin. EST 79-54 was 99% identical to EST 8-40 over 317 bases, while EST 24-31 was 99% identical to EST 8-40 over 257 bases. EST 79-54 and EST 24-31 did not overlap and therefore shared no identity. EST 8-40, however was a longer transcript and thus represented a more complete version of the gene. This clone was used for further analysis.

Gene 2 is represented by 3 ESTs (8-30; GenBank Accession No. BG524852, SEQ ID No. 6, 55-93; GenBank Accession No. BG525998, SEQ ID No. 7, 77-16; SEQ ID No. 8) and has similarity to a cytochrome P450-dependant monooxygenase (CYP701A5, ent-kaurene oxidase from *Stevia rebaudiana*, GenBank Accession No. AAQ63464) that catalyses the three step oxidation of ent-kaurene to ent-kaurenoic acid. ESTs 8-30, 55-93 and 77-16 did not overlap and therefore shared no identity. EST 55-93 however was a longer transcript and thus represented a more complete version of the gene. This clone was used for further analysis.

Gene 3 is represented by 1 EST (17-50; GenBank Accession No. BG522027, SEQ ID No. 9) and has similarity to a cytochrome P450-dependant monooxygenase (CYP71A10 from *Glycine max*, GenBank Accession No. AAB94590) that functions as an N-demethylase with regard to fluometuron, linuron, and diuron, and as a ring-methyl hydroxylase when chlortoluron is the substrate. This clone was used for further analysis.

Gene 4 is represented by 1 EST (52-62, GenBank Accession No. BG525699, SEQ ID No. 10) and has similarity to a cytochrome P450-dependant monooxygenase (CYP720B1, abietadienol/abietadienal oxidase from *Picea sitchensis*, GenBank Accession No. AAX07436) which is a multifunctional, multisubstrate P450 enzyme that catalyzes a number of consecutive oxidation steps with several different diterpenol and diterpenal intermediates. This clone was used for further analysis.

Gene 5 is represented by 3 ESTs (4-67; GenBank Accession No. BG524275, SEQ ID No. 11, 42-55; GenBank Accession No. BG524436, SEQ ID No. 12, 49-53; GenBank Accession No. BG525768, SEQ ID No. 13) and has similarity to several uncharacterized cytochrome P450-dependant monooxygenases (CYP82C1p from *Glycine max*, Genbank Accession No. AAB94590, an elicitor induced P450 from *Glycine max*, GenBank Accession No. CAA71876, and a wound-inducible P450 from *Pisum sativum* (GenBank Accession No. AAG09208). EST 4-67 was 97% identical to EST 42-55 over 318 bases, EST 4-67 was 92% identical to EST 49-53 over 302 bases and EST 42-55 was 94% identical to EST 49-53 over 302 bases. EST 4-67 however was a longer transcript and thus represented a more complete version of the gene. This clone was used for further analysis.

Gene 6 is represented by 2 ESTs (29-6; GenBank Accession No. BG523165, SEQ ID No. 14, 49-88 BG525439, SEQ ID No. 15) and has similarity to a cytochrome P450-dependant monooxygenase (CYP720B1, abietadienol/abietadienal oxidase from *Picea sitchensis*, GenBank Accession No. AAX07436) which is a multifunctional, multisubstrate P450 enzyme that catalyzes a number of consecutive oxidation steps with several different diterpenol and diterpenal intermediates. EST 29-6 is 97% identical to EST 49-88 over 360 bases. EST 29-6 however was a longer transcript and thus represented a more complete version of the gene. This clone was used for further analysis.

The full length translated amino acid sequences for all six genes were determined along with the predicted molecular weights and are as follows:

| Gene (EST) | DNA Sequence | Protein Sequence | Number of amino acids/Predicted molecular weight (kDa) |
|---|---|---|---|
| 1 (8-40) | SEQ ID No. 1 | SEQ ID No. 2 | 528/60.5 |
| 2 (55-93) | SEQ ID No. 16 | SEQ ID No. 17 | 511/57.8 |
| 3 (17-50) | SEQ ID No. 18 | SEQ ID No. 19 | 524/59.7 |
| 4 (52-62) | SEQ ID No. 20 | SEQ ID No. 21 | 476/54.4 |
| 5 (4-67) | SEQ ID No. 22 | SEQ ID No. 23 | 522/59 |
| 6 (29-6) | SEQ ID No. 24 | SEQ ID No. 25 | 525/60.1 |

The translated amino acid sequence for each gene was subjected to a conserved domain search using CD-Search (Machler-Bauer and Bryant. 2004. Nucleic Acids Res. 32: W327-31) and all had a significant alignment with the domain model for cytochrome P450 monooxygenases. The translated amino acid sequence for each gene was scanned using Scan Prosite excluding the motifs with a high probability of occurrence (release 19.11; Hofmann et al. 1999. Nucleic Acids Res. 27:215-219) and all were shown to contain a heme-iron ligand domain at the positions indicated below:

| Gene (EST) | SEQ ID No. | CD bit score (E-value) | heme-iron ligand residue nos. (sequence) |
|---|---|---|---|
| 1 (8-40) | SEQ ID No. 2 | 236 (5e–63) | 469-478 (FGgGPRICIG) |
| 2 (55-93) | SEQ ID No. 17 | 230 (4e–61) | 450-459 (FGgGKRVCAG) |
| 3 (17-50) | SEQ ID No. 19 | 288 (1e–78) | 454-463 (FStGRRMCPA) |
| 4 (52-62) | SEQ ID No. 21 | 167 (2e–42) | 416-425 (FGgGPRMCLG) |
| 5 (4-67) | SEQ ID No. 23 | 262 (1e–70) | 457-466 (FGaGRRYCPG) |
| 6 (29-6) | SEQ ID No. 25 | 178 (2e–45) | 419-428 (FGgGPRMCLG) |

Searches of the GenBank databases, using BLASTP, with the translated full-length sequence of all genes revealed several significant similarities (Altschul et al. 1997. Nucleic Acids Res. 25:3389-3402) with plant and cytochrome P450-dependant monooxygenases. Five matches are given for each gene:

Gene 1 (8-40) had the following matches:

| GenBank Acession Number | Description | Score (bits) | E value |
|---|---|---|---|
| AAA33106 | Cytochrome P-450 protein | 560 | 6.000e–158 |
| AAA17732 | Cytochrome P450 | 558 | 1.000e–157 |

-continued

| GenBank Acession Number | Description | Score (bits) | E value |
|---|---|---|---|
| AAA17746 | Cytochrome P450 | 555 | 1.000e−156 |
| AAL57694 | AT3g14660/MIE1_16 | 553 | 4.000e−156 |
| AAM20382 | putative cytochrome P450 | 551 | 2.000e−155 |

Specifically, the translated cDNA was found to be similar (51% identity) to a *Catharanthus roseus* cytochrome P450-dependant monoxygenase known as secologanin synthase that catalyses oxidative ring cleavage in the synthesis of the terpene indole alkaloid secologanin (Irmler et al. 2000. Plant J. 24:797-804) and several other puative P450 monooxygenases of unknown function.

Gene 2 (55-93) had the following matches:

| GenBank Acession Number | Description | Score (bits) | E value |
|---|---|---|---|
| ABA42921 | kaurene oxidase | 727 | 0 |
| AAY42951 | kaurene oxidase | 724 | 0 |
| AAG41776 | ent-kaurene oxidase | 611 | 2.000e−173 |
| AAP69988 | ent-kaurene oxidase | 601 | 2.000e−170 |
| NP_197962 | GA3 | 594 | 2.000e−168 |

Specifically, the translated cDNA was found to be similar (71% identity) to a *Stevia rebaudiana* cytochrome P450-dependant monoxygenase kaurene oxidase that catalyses three step oxidation of ent-kaurene to ent-kaurenoic acid (Humphrey et al, in press). Other similarities were to genes also encoding ent-kaurene oxidase.

Gene 3 (17-50) had the following matches:

| GenBank Acession Number | Description | Score (bits) | E value |
|---|---|---|---|
| NP_189154 | CYP82G1; heme binding | 504 | 2.000e−141 |
| AAB94590 | CYP82C1p [Glycine max] | 487 | 5.000e−136 |
| CAA71876 | putative cytochrome P450 | 479 | 1.000e−133 |
| NP_194922 | CYP82C4; heme binding | 471 | 2.000e−131 |
| AAC39454 | (S)—N-methylcoclaurine | 470 | 7.000e−131 |

Specifically, the translated cDNA was found to be similar (48% identity) to an *Arabidopsis thaliana* uncharacterized cytochrome P450-dependant monoxygenase. Other similarities were to uncharacterized inducible P450 monooxygenases.

Gene 4 (52-62) had the following matches:

| GenBank Acession Number | Description | Score (bits) | E value |
|---|---|---|---|
| AAX07437 | cytochrome P450 CYPA2 | 469 | 1.000e−130 |
| AAX07436 | cytochrome P450 CYPA1 | 467 | 4.000e−130 |
| NP_198460 | CYP716A1; heme binding | 440 | 6.000e−122 |
| AAL23619 | taxane 13-alpha-hydroxylase | 374 | 4.000e−102 |
| AAX20147 | taxane 13-alpha-hydroxylase | 373 | 1.0000e−101 |

Specifically, the translated cDNA was found to be similar (49% identity) to a *Picea sitchensis* cytochrome P450-dependant monoxygenase known as abietadienol/abietadienal oxidase, which is a multifunctional, multisubstrate P450 enzyme that catalyzes a number of consecutive oxidation steps with several different diterpenol and diterpenal intermediates. Other similarities were to an uncharacterized *Arabidopsis thaliana* P450 and to a *Taxus cuspidata* taxol biosynthesis gene, taxane 13-alpha-hydroxylase (Jennewein et al, 2001. PNAS. 98; 13595-13600).

Gene 5 (4-67) had the following matches:

| GenBank Acession Number | Description | Score (bits) | E value |
|---|---|---|---|
| AAB94590 | CYP82C1p | 468 | 2.000e−130 |
| CAA71876 | putative cytochrome P450 | 448 | 2.000e−124 |
| AAG09208 | wound-inducible P450 | 438 | 3.000e−121 |
| CAA71877 | putative cytochrome P450 | 436 | 1.000e−120 |
| AAC49188 | cytochrome P450 | 436 | 1.000e−120 |

Specifically, the translated cDNA was found to be similar (49% identity) to an uncharacterized *Glycine max* cytochrome P450-dependant monoxygenase. Other similarities were to uncharacterized inducible P450 monooxygenases.

Gene 6 (29-6) had the following matches:

| GenBank Acession Number | Description | Score (bits) | E value |
|---|---|---|---|
| AAX07437 | cytochrome P450 CYPA2 | 466 | 6.000e−130 |
| AAX07436 | cytochrome P450 CYPA1 | 462 | 9.000e−129 |
| NP_198460 | CYP716A1; heme binding | 420 | 7.000e−116 |
| AAL23619 | taxane 13-alpha-hydroxylase | 385 | 2.000e−105 |
| AAX20147 | taxane 13-alpha-hydroxylase | 384 | 3.000e−105 |

Specifically, the translated cDNA was found to be similar (51% identity) to a *Picea sitchensis* cytochrome P450-dependant monoxygenase known as abietadienol/abietadienal oxidase, which is a multifunctional, multisubstrate P450 enzyme that catalyzes a number of consecutive oxidation steps with several different diterpenol and diterpenal intermediates. Other similarities were to an uncharacterized *Arabidopsis thaliana* P450 and to a *Taxus cuspidata* taxol biosynthesis gene, taxane 13-alpha-hydroxylase (Jennewein et al, 2001. PNAS. 98; 13595-13600).

Example 3

Isolation of a Full Length Clones of Ent-Kaurenoic Acid 13-hydroxylase Candidate Genes EST 17-50 and EST 8-40 represented full length cDNAs as determined by the presence of a start codon in a similar position relative to other start codons in known P450 genes. Based on alignments to known P450 monooxygenases the remaining four ESTs represented truncated versions of full length cDNAs at the 5' end. The 5' ends of the genes were obtained using RNA ligase mediated rapid amplification of cDNA ends (RLM-RACE). The procedure was performed on total-RNA freshly isolated from *Stevia* using the FirstChoice RLM-RACE kit (Ambion Inc.) following the manufacturer's instructions. In general, cDNA generated using the kit was used as template in a PCR (outer reaction) with a reverse (or anti-sense) gene specific primer (GSP) and a 5' RACE adapter forward (or sense) primer. The resulting product is used in a second PCR (inner reaction) with a nested GSP and adapter primer and the product is ligated into a t-tailed vector such as pGEM T-easy. Several clones from each reaction are sequenced to identify the 5' end that correctly aligns with the original EST.

Specifically, the forward (or sense) adapter specific primers were the 5' RACE Outer Primer (SEQ ID No. 61) and 5' RACE Inner Primer (SEQ ID No. 62) provided with the FirstChoice RLM-RACE kit (Ambion Inc.). The GSPs were as follows:

| Gene | Outer primer name/SEQ ID No. | inner primer name/SEQ ID No. |
|---|---|---|
| 2 (55-93) | 55-93-1US/SEQ ID No. 63 | 55-93-2US/SEQ ID No. 64 |
| 4 (52-62) | 52-62R1/SEQ ID No. 65 | 52-62R2/SEQ ID No. 66 |
| 5 (4-67) | 4-67-4US/SEQ ID No. 53 | 4-67-7US/SEQ ID No. 67 |
| 6 (29-6) | 29-6 excise US/SEQ ID No. 59 | 29-6-5US//SEQ ID No. 68 |

Finally, to generate a full length cDNA a PCR was performed with two GSPs for each gene using the high fidelity polymerase, Herculase (Stratagene), and template derived from reverse transcribed *Stevia* leaf RNA (ie. cDNA). Gene 1 represented by EST 8-40 had a partial open reading from another gene fused following the 3' untranslated region. To obtain only the full length 8-40 cDNA, PCR was performed using EST 8-40 as a template, the primers 8-40 BamHI-DS (SEQ ID No. 26) and 8-40-1-US (SEQ ID No. 27) and the high fidelity DNA polymerase, Herculase (Stratagene). Gene3 represented by EST 17-50 was a full-length cDNA and did not require PCR amplification. Gene 6 (EST 29-6) was a near full length cDNA missing 6 nucleotides at the 5' end of the open reading frame. A primer 5'29-6 BamHI (SEQ ID No. 28) corresponding to the original clone was synthesized and incorporated the missing 6 nucleotides. To generate a full length cDNA, PCR was performed using EST 29-6 as a template, the primers 5'29-6 BamHI (SEQ ID No. 28) and T7+ (SEQ ID No. 29) and the high fidelity DNA polymerase, Herculase (Stratagene). The primers used for the remaining genes were as follows:

| Gene (EST) | Forward primer/SEQ ID No. | Reverse primer/SEQ ID No. |
|---|---|---|
| 2 (55-93) | 55-93 EcoRI-DS/SEQ ID No. 30 | 55-93 EcoRI-US/SEQ ID No. 31 |
| 4 (52-62) | 52-62 BamHI-F2/SEQ ID No. 32 | 52-62R4/SEQ ID No. 33 |
| 5 (4-67) | 4-67 BamHI-DS/SEQ ID No. 34 | 4-67 EcoRI-US/SEQ ID No. 35 |

All PCR products were ligated in pGEM-T Easy (Promega) and sequenced to ensure errors were not introduced during amplification. The full length genes were completely sequenced using the following primers:
Gene 1 (8-40): 8-40-1US (SEQ ID No. 27), 8-40-2DS (SEQ ID No. 36), 8-40-3US (SEQ ID No. 37), 8-40-4DS (SEQ ID No. 38), T7 (SEQ ID No. 39), SP6 (SEQ ID No. 40).
Gene 2 (55-93): 55-93-3DS (SEQ ID No. 41), 55-93-4US (SEQ ID No. 42), T7, SP6.
Gene 3 (17-50): 17-50-1DS (SEQ ID No. 43), 17-50-3US (SEQ ID No. 44), 17-50-4DS (SEQ ID No. 45), 17-50-5US (SEQ ID No. 46), 17-50-6US (SEQ ID No. 47), T3+(SEQ ID No. 48), T7+.
Gene 4 (52-62): 52-62 F1 (SEQ ID No. 49), 52-62 R1 (SEQ ID No. 50), T7, SP6.
Gene 5 (4-67): 4-67-2US (SEQ ID No. 51), 4-67-3DS (SEQ ID No. 52), 4-67-4US (SEQ ID No. 53), 4-67-5DS (SEQ ID No. 54), T7, SP6.
Gene 6 (29-6): 29-6-1DS (SEQ ID No. 55), 29-6-3DS (SEQ ID No. 56), and 29-6-4US (SEQ ID No. 57), T3+, T7+, M13F (SEQ ID No. 58).

The resulting full length clones were termed: 8-40 (SEQ ID No. 1), 55-93 (SEQ ID No. 16), 17-50 (SEQ ID No. 18), 52-62 (SEQ ID No. 20), 4-67 (SEQ ID No. 22) and 29-6 (SEQ ID No. 24).

A comparison of the full length 29-6 cDNA (SEQ ID No. 24), revealed the presence of a stop codon starting at nucleotide number 1039. Based on sequence comparisons to known genes it was suspected that this clone contained an intron that was not spliced correctly during mRNA processing. In order to test for the presence of an intron two primers (29-6-3DS, SEQ ID No. 59 and 29-6-4US, SEQ ID No. 60) were designed on either side of the suspected intron and used in a PCR with the *Stevia* leaf cDNA library as a template. Only one band was observed when the products were separated by electrophoresis on an agarose gel. The observed size was approximately 620 base pairs as would be expected if the intron was not present. The resulting products were ligated into pBluescript II KS+ and several clones were sequenced. All clones sequenced did not contain the suspected intron sequence, thus supporting the observation that EST 29-6 resulted from incorrect mRNA processing. In order to remove the intron sequence from the 29-6 cDNA a method was developed closely following the ExSite™ PCR-Based Site-Directed Mutagenesis Kit revision #060006a, method (B) (Stratagene). Briefly, two outward facing primers (29-6 excise US, SEQ ID No. 59 and 29-6 excise DS, SEQ ID No. 60) were designed on either side of the fragment to be removed. A PCR was carried out in which the entire vector and insert were amplified without the intron sequence. A methylation sensA ligation reaction was performed followed by a transformation into *E. coli*. Plasmid DNA was prepared from several colonies and sequenced. One plasmid was identified as containing the full length cDNA for Gene 6 without the intron found in the original clone, it was labelled 29-6-C (SEQ ID No. 24).

Example 4 cDNA Cloning into Plant and Yeast Expression Vectors

The full length cDNAs were digested from pGEM-T Easy vector (Promega), or in the case of 29-6 the pBluescript KS+ vector, using the following enzymes: BamHI and EcoRI for 8-40, 4-67, 29-6 and 52-62, BamHI and KpnI for 17-50 and EcoRI for 55-93. The digested DNA was separated by electrophoresis in an agarose gel and the band corresponding to the insert was cut out. The DNA was removed from the gel using the Prep-A-Gene gel purification kit (BioRad) and ligated into the BamHI/EcoRI, or BamHI/KpnI or EcoRI sites of the pYed60 vector (Pompon) for expression in yeast, or the pCaMterX vector (Menassa, R.; Nguyen, V,; Jevnikar, A M,; Brandle, J E; (2001) Molecular Breeding 8:177-185) for expression in plants. One microliter of each ligation reaction was used for transforming *E. Coli* strain XL1-Blue MRF' cells (Stratagene). Positive colonies were identified using a PCR screening method with gene specific and vector specific primers.

Example 5 cDNA Expression in Yeast

Yeast Transformation

The pYeD60 constructs were transformed into the Wat11 and Wat21 yeast cell lines (Pompon). A single colony of yeast from each strain was picked using a sterile loop from a YPGA plate (20 g/l glucose, 10 g/l yeast extract, 10 g/l bactopeptone, 30 mg/l adenine, 20 g/l agar) and used to inoculate 20 ml of liquid SC-U medium (1.7 g/l yeast nitrogen base, 5 g/l ammonium sulfate, 0.77 g/l complete supplement mixture (amino acids) without uracil, 20 g/l glucose). The culture was grown 48 h at 30 C and 225 rpm until an OD600 of 3.2 was reached. Six millimeters of culture was added to 44 ml of YPGA liquid media (20 g/l glucose, 10 g/l yeast extract, 10 g/l bactopeptone, 30 mg/l adenine) to make 50 ml of culture at an OD600 of 0.4. This was grown for 3 h at 30EC and 225 rpm.

The cells were washed by pelleting them at 1500×g for 15 min at room temperature and resuspending them in 40 ml of 1×TE (10 mM Tris (pH 7.5), 1 mM EDTA (ethylenediaminetetraacetic acid)). The cells were pelleted at 1500×g for 15 min at room temperature, resuspended in 2 ml of 1×LiAc/ 0.5×TE (100 mM LiAc (pH 7.5), 5 mM Tris (pH 7.5), 0.5 mM EDTA) and incubated at room temperature for 10 minutes.

For each transformation 1 µg of plasmid DNA and 100 µg of denatured sheared salmon sperm DNA was mixed with 100 µl of the yeast suspension from above. 700 µl of 1×LiAc/40% PEG-3350/1×TE (100 mM LiAc (pH 7.5), 400 g/l PEG-3350 (polyethylene glycol), 5 mM Tris (pH 7.5), 0.5 mM EDTA) was added, mixed and the tubes were incubated at 30EC for 30 minutes. 88 µl of DMSO (dimethyl sulfoxide) was added, mixed and the transformations were heat shocked at 42 C for 7 minutes. The transformations were centrifuged in a microcentrifuge for 10 s and the supernatant was removed. The cell pellets were resuspended in 1×TE and re-pelleted. Finally the cell pellets were resuspended in 100 µl of 1×TE and 50 µl was plated on to SC-U (1.7 g/l yeast nitrogen base, 5 g/l ammonium sulfate, 0.77 g/l complete supplement mixture (amino acids) without uracil, 20 µl glucose, 20 g/l agar) selective plates and grown for 3 days at 30EC. Several colonies from each transformation picked and placed in 50 µl of SC-U liquid media. PCR analyses were performed to identify which ones contained the plasmid. A single colony was chosen for each construct and used in subsequent experiments.

Yeast Expression

Yeast containing each of genes 1-6, were streaked on to selective plates (SC-U) and grown 48 h at 30EC. A single colony from each plate was picked using a sterile loop and added to 3 ml of SC-U and grown 30 h at 30 C and 225 rpm. One milliliter of each culture was used to inoculate 25 ml of SC-U and grown for 24 h at 30 C and 225 rpm. The culture was pelleted by centrifugation at 1500×g and resuspended in 5 ml of YPI (medium) which was added to 20 ml of YPI (10 g/l yeast extract, 10 g/l bactopeptone, 20 g/l galactose) medium and grown for 16 h at 30EC and 225 rpm. Analysis of expression cultures by SDS polyacrylamide gel electrophoresis (SDS-PAGE) revealed all P450 monooxygenases were expressed in both yeast strains except for 29-6 which did not appear to be expressing protein in either yeast strain.

Example 6

Ent-Kaurenoic Acid 13-Hydroxylase Analysis

For each gene 5 ml of expression culture was pelleted and resuspended in 1 ml of kaurenoic acid assay buffer (100 mM Tris (pH 7.5), 1 mM DTT (dithiothreotol), 0.5 mM NADPH (nicotinamide adenine dinucleotide phosphate), 0.5 mM FAD (flavin-adenine dinucleotide), 0.05 mg/ml kaurenoic acid, 0.05× Complete EDTA-free protease inhibitor cocktail (Roche), 0.4 µM PMSF (phenylmethylsulphonylfluoride)) and incubated at 30° C. for 5 h at 850 rpm in an Eppendorf Thermomixer (Westbury, N.Y.).

The culture was pelleted and the supernatant was collected and analysed by reverse-phase chromatography (C18) and negative ion ESI-MS for the presence of steviol. The analyses were done isocratically with 90:10 methanol-water. Steviol eluted at ca. 4.5 min. Three constructs were identified as having the ability to convert kaurenoic acid to steviol, however only 8-40 showed an appreciable amount of accumulation and worked with both Wat11 and Wat21. The peak heights observed for kaurenoic acid and steviol in 10 µL of the samples based on the ion intensity within 0.01 Da of the masses for [M-H]− ions of 301.75 and 317.74 Da, respectively, were as follows:

| Gene  | yeast strain | steviol peak height |
|-------|--------------|---------------------|
| 8-40  | Wat11        | 11                  |
| 8-40  | Wat21        | 207                 |
| 55-93 | Wat11        | —                   |
| 55-93 | Wat21        | 10                  |
| 17-50 | Wat11        | 10                  |
| 17-50 | Wat21        | —                   |
| 52-62 | Wat11        | —                   |
| 52-62 | Wat21        | —                   |
| 4-67  | Wat11        | —                   |
| 4-67  | Wat21        | —                   |

Example 7 cDNA Expression in Plants

Constructs generated in the pCaMterX vector were transformed into *Agrobacterium tumafaciens* (strain LBA4404) via electroporation. Colonies were screened by PCR to determine which ones contained the construct. Bacteria from each strain were streaked onto LB plates containing 50 µg/ml rifampicin, 30 µg/ml streptomycin, and 50 µg/ml kanamycin and grown for 3 days at 28 C. A 3 ml LB culture with antibiotics was inoculated with a single colony and grown overnight at 28C and 225 rpm. One milliliter of overnight culture was used to inoculate 100 ml of LB with 50 µg/ml kanamycin and grown until an OD600 between 0.5 and 1.2 was reached (approximately 18-24 h).

The culture was pelleted at 3000 g for 15 min at 4C then resuspended in freshly made 5% sucrose solution to an OD600 of 0.8. Silwet L-77 (Lehle Seeds) was added to a final concentration of 0.02% v/v. The resuspended culture was poured into a shallow container and the above ground parts of 47 day old *Arabidopsis* plants were submerged and agitated gently for 3 seconds. Plants were placed under a clear plastic cover for 24 h and the transformation was repeated 7 days later.

Seeds were collected upon maturity and approximately 1000 of each construct were plated on ½ MS with 50 µg/ml kanamycin to screen for transformants. After 14 days seedlings appearing green were transferred to soil and grown to maturity (designated as T1 plants). Leaf tissue was collected and DNA isolated to check for the presence of the transgene by PCR. Plants identified as containing the transgene were grown to maturity and seed were collected (designated T2 seed). From ten plants of each construct approximately 200 T2 seed were plated on ½ MS with 50 µg/ml kanamycin to determine transgene copy number. Seed exhibiting a 3 to 1 ratio of kanamycin resistant to susceptible were determined to be single copy. From these plates 10 plantlets were transferred to soil and grown to maturity. Seed collected from these plants were analyzed to determine which lines were homozygous.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. An isolated nucleotide sequence encoding an ent-kaurenoic acid 13-hydroxylase polypeptide defined by SEQ ID NO: 2.

2. A nucleotide construct comprising the nucleotide sequence of claim 1.

3. The nucleotide construct of claim 2, wherein said construct is an expression vector.

4. A cell comprising the nucleotide construct of claim 2.

5. The cell of claim 4, wherein said cell is a plant cell, yeast cell, bacterial cell or mammalian cell.

* * * * *

SEQUENCE LISTING

<160> NUMBER OF SEQ ID NOS: 68

<210> SEQ ID NO 1
<211> LENGTH: 1569
<212> TYPE: DNA
<213> ORGANISM: Stevia rebaudiana

<400> SEQUENCE: 1

```
atgggtctct tccctttgga agatagttac gcactcgtct ttgaaggttt agcaataact      60
ctagctctct actacttatt atccttcatc tataaaacct ctaaaaagac ttgtactcca     120
cctaaagcaa gcggtgagca ccctataaca ggccacttaa accttcttag tggttcatcc     180
ggtcttcccc atctagcctt agcatctttg gctgaccgat gtgggcccat attcaccatc     240
cgacttggca tacgtagagt tttggtggtt agtaattggg aaattgctaa ggagatcttc     300
actacccatg atttgattgt ttcaaaccgt cccaaatacc tcgctgcaaa gattttggga     360
ttcaactatg tgtccttttc gtttgctcca tatggcccct attgggttgg aatccgtaag     420
atcatcgcca caaaactgat gtcaagtagc aggctccaga agcttcagtt tgtccgagtt     480
ttcgaactag aaaactccat gaaaagcata cgcgagtctt ggaaagagaa aaaagacgaa     540
gaaggtaaag tgttggtgga gatgaaaaaa tggttttggg aattgaatat gaatatagtt     600
cttagaactg ttgctggtaa acagtacact ggaactgttg atgatgcgga tgcgaagagg     660
attagtgaat tgtttagaga atggtttcat tacacaggaa ggtttgttgt gggagatgct     720
tttcctttc ttgggtggtt ggatttgggt ggatataaga agaccatgga actagtggct     780
tccagactag attccatggt ctcaaaatgg ttagacgagc atcgcaaaaa gcaggctaac     840
gacgacaaaa agaggacat ggatttcatg gacatcatga tatcgatgac tgaagccaat     900
tccccttggg agggttatgg tacgatacaa taattaaaa ccacttgcat gactcttatt     960
gtcagtggtg tagatacaac ctccatcgtg ctaacttggg cactctcgtt actactgaac    1020
aaccgtgaca ctcttaagaa agctcaagaa gagctagaca tgtgtgtggg aaaaggtcga    1080
caagtaaacg aatcagatct agtaaaccta atctaccttg aagccgtatt aaaagaagca    1140
ttgcgactat acccagcagc attccttgga ggtcctagag ccttttagaa agactgcacc    1200
gtggcagggt accgtatccc aaaaggcaca tgtctactta ttaacatgtg aaacttcat     1260
cgtgatccaa acatatggtc agacccatgt gagtttaaac cagagaggtt cttaacccca    1320
aaccaaaagg acgtagatgt tattggaatg gatttttgagt taatcccatt tggtgcggga    1380
agaaggtatt gtccagggac acgtttggca ttacaaatgt tacacatagt tctggccact    1440
ctactacaaa actttgagat gtcaactcca aatgatgcac ccgttgatat gaccgcgagt    1500
gttggaatga caaatgcgaa ggcaagtcca cttgaagttc tactttcgcc acgtgttaag    1560
tggtcatag                                                           1569
```

<210> SEQ ID NO 2
<211> LENGTH: 522
<212> TYPE: PRT
<213> ORGANISM: Stevia rebaudiana

<400> SEQUENCE: 2

```
Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Leu Ser Phe Ile Tyr Lys
            20                  25                  30
```

```
Thr Ser Lys Lys Thr Cys Thr Pro Pro Lys Ala Ser Gly Glu His Pro
         35                  40                  45

Ile Thr Gly His Leu Asn Leu Leu Ser Gly Ser Ser Gly Leu Pro His
 50                  55                  60

Leu Ala Leu Ala Ser Leu Ala Asp Arg Cys Gly Pro Ile Phe Thr Ile
 65                  70                  75                  80

Arg Leu Gly Ile Arg Arg Val Leu Val Val Ser Asn Trp Glu Ile Ala
                 85                  90                  95

Lys Glu Ile Phe Thr Thr His Asp Leu Ile Val Ser Asn Arg Pro Lys
                100                 105                 110

Tyr Leu Ala Ala Lys Ile Leu Gly Phe Asn Tyr Val Ser Phe Ser Phe
                115                 120                 125

Ala Pro Tyr Gly Pro Tyr Trp Val Gly Ile Arg Lys Ile Ile Ala Thr
130                 135                 140

Lys Leu Met Ser Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
                180                 185                 190

Trp Glu Leu Asn Met Asn Ile Val Leu Arg Thr Val Ala Gly Lys Gln
                195                 200                 205

Tyr Thr Gly Thr Val Asp Asp Ala Asp Ala Lys Arg Ile Ser Glu Leu
210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255

Glu Leu Val Ala Ser Arg Leu Asp Ser Met Val Ser Lys Trp Leu Asp
                260                 265                 270

Glu His Arg Lys Lys Gln Ala Asn Asp Lys Lys Glu Asp Met Asp
                275                 280                 285

Phe Met Asp Ile Met Ile Ser Met Thr Glu Ala Asn Ser Pro Leu Glu
290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
                325                 330                 335

Leu Leu Leu Asn Asn Arg Asp Thr Leu Lys Lys Ala Gln Glu Glu Leu
                340                 345                 350

Asp Met Cys Val Gly Lys Gly Arg Gln Val Asn Glu Ser Asp Leu Val
                355                 360                 365

Asn Leu Ile Tyr Leu Glu Ala Val Leu Lys Glu Ala Leu Arg Leu Tyr
370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
                405                 410                 415

Trp Lys Leu His Arg Asp Pro Asn Ile Trp Ser Asp Pro Cys Glu Phe
                420                 425                 430

Lys Pro Glu Arg Phe Leu Thr Pro Asn Gln Lys Asp Val Asp Val Ile
                435                 440                 445

Gly Met Asp Phe Glu Leu Ile Pro Phe Gly Ala Gly Arg Arg Tyr Cys
450                 455                 460
```

```
Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
            485                 490                 495

Met Thr Ala Ser Val Gly Met Thr Asn Ala Lys Ala Ser Pro Leu Glu
        500                 505                 510

Val Leu Leu Ser Pro Arg Val Lys Trp Ser
        515                 520

<210> SEQ ID NO 3
<211> LENGTH: 621
<212> TYPE: DNA
<213> ORGANISM: Stevia rebaudiana
<220> FEATURE:
<221> NAME/KEY: misc_feature
<222> LOCATION: (15)..(15)
<223> OTHER INFORMATION: n is a, c, g, or t

<400> SEQUENCE: 3
accagcaatc ttttngtcag agtttgaccg gactcttctt cgggagcatt ggaaccgagc      60
tagctcattt ccccactcct cctgctctca catcccctt ttggttgtgg ttggtgacat     120
ggcatttggg actctttatt tgcctcactt ttgggcaaat tggttcaaa ggaaggaccg     180 aagattattt tgagaagtaa atccatgtat ctgaaattta ttttagttct tgatctttgt     240
tgtttgtgtc taaatatccc ttatgaaatt caaaagtttt tcttgtaccc acgaagccat     300
ggagagaact acagtttctt gtgttgttgg agttgcaaca atcttgttgt tttacatatg     360
gaagatttca aatcggttgt ggttcaaacc aaagaagatt gagaaatttc taagagatca     420
aggactcaaa ggtacctctt ataaattcat ttacggagat atgaaagaga tggcacaaac     480
gatgcacgaa tccaggtcta aacccatggc tctaactcac gatattgctc cacgtgtcac     540
gcccttcttc cacaaatccg caccactttt ggtaagacat gttttacatg gatgggaaca     600
aaacctatgg acatatatgt g                                                621

<210> SEQ ID NO 4
<211> LENGTH: 570
<212> TYPE: DNA
<213> ORGANISM: Stevia rebaudiana
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t

<400> SEQUENCE: 4
acaatggccg cagcaacctc caccgtcgtg ggtttggcca cgtcctccct ctcatcaccg      60
tcttcagtca accgcaaaca acccgcctta aactcagcct tcttgaagtc tccgatgaca     120
gcaaggaacc ctttgaaggt ttcacaagct tcaggtggca aatatacatg ttttgaacga     180
gactggctac gcaaagactt gaatgtgatc gggtttgggt tgatcgggtg gctcgcacca     240
tcgagcatac cagcaatcaa cggtcagagt ttgaccggac tcttcttcgg gagcattgga     300
accgagctag ctcatttccc cactcctcct gctctcacat ccccctttg ttgtggttg     360 gtgacatggc atttgggact ctttatttgc ctcacttttg gcaaattgg gttcaaagga     420 aggaccgaag attattttga gaagtaaatc catgtatctg aaatttattt tagttcttga     480
tctttgttgn ttgtgtctaa atatcccctta tgaaattcat gggttatcta atctttatat     540
```

```
gatgtaatat atctnctact cttccattaa                                      570
```

<210> SEQ ID NO 5
<211> LENGTH: 320
<212> TYPE: DNA
<213> ORGANISM: Stevia rebaudiana

<400> SEQUENCE: 5

```
ataacaaaaa gttttcttgt acccacgaag ccatggagac aactacagtt tcttgtgttg      60
ttggagttgc aacaatcttg ttgtttaca tatggaagat ttcaaatcgg ttgtggttca     120
aaccaaagaa gattgagaaa tttctaagag atcaaggact caaaggtacc tcttataaat    180
tcatttacgg agatatgaaa gagatggcac aaacgatgca cgaatccagg tctaaaccca    240
tggctctaac tcacgatatt gctccacgtg tcacgcccett cttccacaaa tccgtcacga    300
cttttggtaa gacatgtttt                                                320
```

<210> SEQ ID NO 6
<211> LENGTH: 620
<212> TYPE: DNA
<213> ORGANISM: Stevia rebaudiana
<220> FEATURE:
<221> NAME/KEY: misc_feature
<222> LOCATION: (525)..(525)
<223> OTHER INFORMATION: n is a, c, g, or t

<400> SEQUENCE: 6

```
accagacaaa aattcccact tttgaaagta ccacattcat tatggtgatt aatcctaaaa      60
gaccatacgg caaaatccaa ccatatatcc atcctttat ttcctagatt tctaacagtt     120
catatttcat aacaacaaaa caagattcta tgcgattaat cgattatcct taaatcattc    180
ccgtttagtg ggttgctgcg gccaccaacg ccatatgctc gatcaaatcc aacacgcggt    240
tgctgtaacc ccactcattg tcgtaccacg ataccaactt cacaaatgat gcacttagcc    300
ctattccagc ttttgcatca aaaatacttg atctggaatc accaacaaag tcattggaga    360
cgacatctct cgtgccgaat tcggcacgag atcgacttgc aaagaacgat ggcgtttggt    420
gggggggaaac gggtttgtgc tggggctatg caggcgatgt tgatcgcgtg tgcgtctatt    480
ggtagaatgg tgcgcgagtt cgagtggaga cttaaagatg atacnggtga agatgttaat    540
acgcttgggg cttactacac agaaacttaa tccgatgctt gcagttatta agcccagaaa    600
ttaataatta ataataatta                                                620
```

<210> SEQ ID NO 7
<211> LENGTH: 381
<212> TYPE: DNA
<213> ORGANISM: Stevia rebaudiana
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature

```
<222> LOCATION: (290)..(290)
<223> OTHER INFORMATION: n is a, c, g, or t
<220> FEATURE:
<221> NAME/KEY: misc_feature
<222> LOCATION: (316)..(317)
<223> OTHER INFORMATION: n is a, c, g, or t
<220> FEATURE:
<221> NAME/KEY: misc_feature
<222> LOCATION: (379)..(380)
<223> OTHER INFORMATION: n is a, c, g, or t

<400> SEQUENCE: 7
gttgccggtg gtatttctct attgnncctc aaaagttttc tttcaaatca aaatcagcat      60
catcgcggtg gtggtaatta ccgttctgtt cctgaggtac caggattgcc aattgtaggg     120
aacctacttg agttgaagga gaagaaacca tacaagactt ttacaaaatg ggcagaaact     180
tatggtccta tttattccat taaaactgga gccacctcca tggttgttat caactccaat     240
gatatagctn aagaggcttt nttaccaaat ttcnactcaa tttcaacatn ggaagctttc     300
aaaggcatcg aagatnntca ctgctgataa aaccatggta agccatgagt gattatgacc     360
gattattcac aagactggnn a                                               381

<210> SEQ ID NO 8
<211> LENGTH: 228
<212> TYPE: DNA
<213> ORGANISM: Stevia rebaudiana

<400> SEQUENCE: 8
cagctacatt gattacttgt tatctgatgc acaaccgtta actgatctac aactcctaat      60
gtcactctgg gaaccgatta ttgaaacagc agacactaca atggtcacaa cagaatgggc     120
aatgtatgaa cttgcaaaaa acccagagaa acagacccgt ctgtttaacg aagtccaaag     180
cgtttgcggg tcagaacaaa tcacagagga aaagttatgt aaaatgcc                  228

<210> SEQ ID NO 9
<211> LENGTH: 644
<212> TYPE: DNA
<213> ORGANISM: Stevia rebaudiana

<400> SEQUENCE: 9
agagatacaa attaaatatg gtggcttttc ctcaatttct atcattttta gggcttctac      60
tttttgttat atcctatagt tacaatataa gaaaagaag taacacaaaa agaagtatta     120
aacctaaagc tcctgaacct tcaggggcat gccttttat aggccacctc cattttctaa     180
gaagtcaagt tcctttagca aggatatttg gaaagattgc tgacgactac gggccggttt     240
actctttacg gctcggtttt cgtcaagcat tggttgtaag cagttggcag atggtcaaag     300
aatgtttcac cacaaatgac aaaaactttg caaccagacc caacatggca attagccggc     360
acatggtcta caacaatgct ggttttgcac tcgcgccata tggaccatat tggcgagaga     420
tccgaaagat tgttgcttcc gagctttta catcccaacg tgttgaaaag ttcatgaatg     480
ttcgtgactc agaagtgaaa aactctatta acgagctcta tttgttgtcc tcaaagaagg     540
cgaacggatc atcgattgtg gaaatgaaca agtggtttga ccacataacg ttcaatataa     600
ttataagaat cttagcgggg aaaagattat taatggttgt aatg                      644

<210> SEQ ID NO 10
<211> LENGTH: 621
<212> TYPE: DNA
<213> ORGANISM: Stevia rebaudiana
<220> FEATURE:
<221> NAME/KEY: misc_feature
```

```
<222> LOCATION: (400)..(400)
<223> OTHER INFORMATION: n is a, c, g, or t

<400> SEQUENCE: 10
ttttttacag cagaaaattt actaattata catttatgtt tcatgtcaca taaaacatta       60
atagattcag ttacttacag gcacaaatta cataagttgt agaataacac aattttattt      120
atcataactt cttcatgcca taaaaacaca taatctgtaa ctaccatgaa gatccattat      180
ggtttacctt cacttcactg attcatgctt gaagtaatca aacttgatgg ggatgaagac      240
gaattggaag cccctttgct ggggtagcca tgggatcata ttctattttc tcatcaggta      300
tcaacaggtc ccatttgaaa ttggtgacaa tattgtgaaa gaaacgcaag tacttccaat      360
cgagcaaatt cttttcctaa acacattcta ggccccccctn caaacggaac aaaggtgaat      420
ggagtcggtc ctgcgccttc aaaccgtgat gggtcaaaac gtgttaccgt cttcaaagtt      480
agcctcgtcc ctttgtgtcg atacagcact ccagtgtagc ttccatcctt tcgggatggt      540
ataacccgca taatcaatat ccacaagggc ctctctatag gttcctataa caggtggatt      600
tagtctcatg acttcacata t                                                621

<210> SEQ ID NO 11
<211> LENGTH: 325
<212> TYPE: DNA
<213> ORGANISM: Stevia rebaudiana
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t

<400> SEQUENCE: 11
tttgattgtt tcaaaccgtc ccaaatcctc gctgcaaaga ttttgggatt caactatgtg       60
tccttttcgt ttgctccata tggcccctat tgggttggaa tccgtaagat catcgccaca      120
aaactgatgt caagtagcag gctccagaag cttcagtttg tccgagtttt cgaactagaa      180
aactccntga aaagcntncg cgagtnttgg aaagagaaaa angacgaaga aggtaaagtg      240
ttggtggaga tgaaaaantg gttttgggaa ttgaatatga atatagttct tagaactgtn      300
gctggtaaac agtcactgga actgt                                            325

<210> SEQ ID NO 12
<211> LENGTH: 579
<212> TYPE: DNA
<213> ORGANISM: Stevia rebaudiana
```

<400> SEQUENCE: 12

```
aagaaatttc atagatgtaa cgactcttct ggtgtgcaat cttgaaaatt ggccacaaag    60
cctcacattt tctcttcccg tcatgtggat cattctcagc ttctctcatc ttagcttgta   120
gttcactgag tgttggctcc acgagttccc agccatccgg atacttgacc cgattcgtct   180
tcaccttagg catatttctg ttcaaaccgt cccaaatacc tcgctgcaaa gattttggga   240
ttcaactatg tgtccttttc gtttgctcca tatggcccct attgggttgg aatccgtaag   300
atcatcgcca caaaactgat gtcaagtagc aggctccaga agcttcagtt tgtccgagtt   360
ttcgaactag aaaactccat gaaaagcata cgcgagtctt ggaaagagaa aaaagacgaa   420
gaaggtaaag tgttggtgga gatgaaaaaa tggttttggg aattgaatat gaatatagtt   480
cttagaactg ttgctggtaa acagtacact ggaactgttg atgatgcgga tgcgaagagg   540
attagtgaat tgtttagaga atggttcatt acacaggaa                          579
```

<210> SEQ ID NO 13
<211> LENGTH: 606
<212> TYPE: DNA
<213> ORGANISM: Stevia rebaudiana
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t

<400> SEQUENCE: 13

```
acacactcgt ctttgaaggt ttancaataa ctctagctct ctactactta ttatccttca    60
tctataaaac ctctaaaaag acttgnactc cacctaaagc aagcggtgag caccctataa   120
caggccactt aaaccttctt agtggttcat ccggtcttcc ccatctagcc ttagcatctt   180
```

-continued
tggctgaccg atgtgggccc atattcacca tccgacttgg catacgtaga gttttggtgg 240
ttagtaattg ggaaattgct aaggagatct tcactaccca tgatttgatt gtttcaaacc 300
gtcccaaata cctcgctgca aagattttgg gattcaacta tgtgtccttt tcgtttgctc 360
catatggccc ctattgggtt ggaatccgtt agatcatngc cacaaaactg atgncaagtn 420
gcaggctcca naagcttcag tttgtccgag ttttctgaac tanaaaactc catgaaaagc 480
atacgccgag tcttggaang agaaaaaaga cgaagaaggt caaagctgtt ggtgnagatg 540
aaaaaatggt ttttgggaat tgaatntgaa tataagttct tagaaactgt tgcttgntaa 600
acagac 606

<210> SEQ ID NO 14
<211> LENGTH: 504
<212> TYPE: DNA
<213> ORGANISM: Stevia rebaudiana
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t

<400> SEQUENCE: 14
ttcangctng ttctaacacc gatcatcctc ttcatcatta tctacgtttt ctggaacgtt 60
tataagaacc agaaatcggn aagaaacaaa ntcaaacttc caccgggaag cttcggatgg 120
ccgtttgtgg gcgaaactct cgccatgcta cgtgcaaatt gggacggagt gccggaaaga 180
ttcgtcaaag aacggatcga gaaacacgga aaccctcaag tgtttaaaac gtcgttgttt 240
ggcgaccgta tggcggtgtt gtgtggacct gctggaaaca agtttctgtt tggtaacgag 300
aacaagctgg tggcggtgtg gtggccgttg cccggtgang aagcttttcg gcaagtgtct 360
gattacaacc cgtggggatg aanctaagtg gatgacgaag atgctgttat cgtatcttgg 420
tcctgatgct ttccaattca ttatgccngc cccatggata ttcgtcaccc gtcggcatat 480
cgacgttcnt tggcgaggcn agaa 504

```
<210> SEQ ID NO 15
<211> LENGTH: 628
<212> TYPE: DNA
<213> ORGANISM: Stevia rebaudiana
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t

<400> SEQUENCE: 15
cgaaacaatg gcactgctac gtgcaaattg ggacggagtg ccggaaagat tcgtcaaaga      60
ncggatcgag aaacacggaa accctcaagt gtttaaaacg tcgttgtttg gcgaccgtat     120
ggcggtgttg tgtggacctg ctggaaacaa gtttctgttt ggtaacgaga caagctggt     180 ggcggtgtgg tggccgttgc cggtgaggaa gcttttcggc aagtgtctga ttacaacccg     240
tggggatgaa gctaagtgga tgaggaagat gctgttatcg tatcttggtc ctgatgcttt     300
cgcaattcat tatgccgtca ccatggatat cgtcacccgt cggcatatcg acgttcattg     360
gcgaggcaag aaagaggtga atgtgttcca aactattaag ttatatgcct ttgagcttgc     420
atgcagttta ttcatgagct tggaggaccc aaatcacatt gcaaaacttg ctttcttgtt     480
taacattttc ttgaaaggcg tgatttgagc ttccaatcaa cgtcccgggg acacgatttt     540
tatagcttcc aacaaaagcc gggagcatct attctgacca aactacaaac aattatcaaa     600
gcaagaaana caagacttga aagangga                                        628

<210> SEQ ID NO 16
<211> LENGTH: 1536
<212> TYPE: DNA
<213> ORGANISM: Stevia rebaudiana

<400> SEQUENCE: 16
atggatgtgc aaacggcggg atcagcggca gtagcattcg gtggtccggt ggcagccgtt      60
gccggtggta tttctctatt gttcctcaaa agttttcttt caaatcaaaa tcagcatcag     120
cgcggtggtg gtaatttccg ttctgttcct gaggtaccag gattgccaat gtagggaac     180 ctacttgagt tgaaggagaa gaaaccatac aagactttta caaatgggc agaaacttat     240 ggtcctattt attccattaa aactggagcc acctccatgg ttgttatcaa ctccaatgat     300
atagctaaag aggcttttgt taccaaattc gactcaattt caacaaggaa gctttcaaag     360
gcattgaaga ttctcactgc tgataaaacc atggtagcca tgagtgatta tgacgattat     420
cacaagactg tcaaacgtaa tttactcact agtatcctag gaccagctgc tatgaagaaa     480 caccgttttcc atagagacac attggcggaa atctatctta accgacttca tgatctggcc     540
ccaaattctc ctcacgaagc tataaacctc cgggagagtt tcagtctga acttttcaca     600 ttagcaatga aacaaacatt tgggagggat ttggaaagca tttacgtggg tgatcttgga     660
accaccatga caagagatga ggtatttcag attttggtgc ttgacccgat gatgggtgca     720
atagaagttg attggagaga cttcttcccg tatctgtctt ggatcccaaa cgaaagcttc     780
gagaagaaaa tcgaacagat gtatatccgt agagaagctg ttatgaaagc acttattcaa     840
gaacacaaaa aacgcataga ttccggagag aatctaaaca gctacattga ttacttgtta     900
tctgatgcac aaccgttaac tgatctacaa ctcctaatgt cactctggga accgattatt     960
```

```
gaaacagcag acactacaat ggtcacaaca gaatgggcaa tgtatgaact tgcaaaaaac    1020
ccagagaaac agaccgtct gtttaacgaa gtccaaagcg tttgcgggtc agaacaaatc    1080
acagaggaaa agttatgtaa aatgccgtac ttattagcgg ttttcatga aaccttgaga    1140 agacatagtc ccgtttcgat aatcccatta agatacgtgc atgaaaacac agagcttgga    1200
gggtaccatg ttccttctgg aaccgagctg gctataaaca tttacgggtg taatatggag    1260
cgtgaaatct gggaggatcc ggaagagtgg aacccggaaa gatttttatc agaaaaggaa    1320
ccgatcgact tgcaaagaac gatggcgttt ggtgggggga acgggtttg tgctggggct    1380 atgcaggcga tgttgatcgc gtgtgcgtct attggtagaa tggtgcgcga gttcgagtgg    1440
agacttaaag atgatacggg tgaagatgtt aatacgcttg gcttactac acagaaactt    1500 aatccgatgc ttgcagttat taagcccaga aattaa                             1536

<210> SEQ ID NO 17
<211> LENGTH: 510
<212> TYPE: PRT
<213> ORGANISM: Stevia rebaudiana

<400> SEQUENCE: 17

Met Asp Val Gln Thr Ala Gly Ser Ala Ala Val Ala Phe Gly Gly Pro
1               5                   10                  15

Val Ala Ala Val Ala Gly Gly Ile Ser Leu Leu Phe Leu Lys Ser Phe
            20                  25                  30

Leu Ser Asn Gln Asn Gln His Gln Arg Gly Gly Gly Asn Phe Arg Ser
        35                  40                  45

Val Pro Glu Val Pro Gly Leu Pro Ile Val Gly Asn Leu Leu Glu Leu
    50                  55                  60

Lys Glu Lys Lys Pro Tyr Lys Thr Phe Thr Lys Trp Ala Glu Thr Tyr
65                  70                  75                  80

Gly Pro Ile Tyr Ser Ile Lys Thr Gly Ala Thr Ser Met Val Val Ile
                85                  90                  95

Asn Ser Asn Asp Ile Ala Lys Glu Ala Phe Val Thr Lys Phe Asp Ser
            100                 105                 110

Ile Ser Thr Arg Lys Leu Ser Lys Ala Leu Lys Ile Leu Thr Ala Asp
        115                 120                 125

Lys Thr Met Val Ala Met Ser Asp Tyr Asp Asp Tyr His Lys Thr Val
    130                 135                 140

Lys Arg Asn Leu Leu Thr Ser Ile Leu Gly Pro Ala Ala Met Lys His
145                 150                 155                 160

Arg Phe His Arg Asp Thr Leu Ala Glu Asn Leu Ser Asn Arg Leu His
                165                 170                 175

Asp Leu Ala Pro Asn Ser Pro His Glu Ala Ile Asn Leu Arg Glu Ser
            180                 185                 190

Phe Gln Ser Glu Leu Phe Thr Leu Ala Met Lys Gln Thr Phe Gly Arg
        195                 200                 205

Asp Leu Glu Ser Ile Tyr Val Gly Asp Leu Gly Thr Thr Met Thr Arg
    210                 215                 220

Asp Glu Val Phe Gln Ile Leu Val Leu Asp Pro Met Met Gly Ala Ile
225                 230                 235                 240

Glu Val Asp Trp Arg Asp Phe Phe Pro Tyr Leu Ser Trp Ile Pro Asn
                245                 250                 255

Glu Ser Phe Glu Lys Lys Ile Glu Gln Met Tyr Ile Arg Arg Glu Ala
            260                 265                 270
```

```
Val Met Lys Ala Leu Ile Gln Glu His Lys Lys Arg Ile Asp Ser Gly
        275                 280                 285

Glu Asn Leu Asn Ser Tyr Ile Asp Tyr Leu Leu Ser Asp Ala Gln Pro
    290                 295                 300

Leu Thr Asp Leu Gln Leu Leu Met Ser Leu Trp Glu Pro Ile Ile Glu
305                 310                 315                 320

Thr Ala Asp Thr Thr Met Val Thr Thr Glu Trp Ala Met Tyr Glu Leu
                325                 330                 335

Ala Lys Asn Pro Glu Lys Gln Thr Arg Leu Phe Asn Glu Val Gln Ser
                340                 345                 350

Val Cys Gly Ser Glu Gln Ile Thr Glu Glu Lys Leu Cys Lys Met Pro
            355                 360                 365

Tyr Leu Leu Ala Val Phe His Glu Thr Leu Arg Arg His Ser Pro Val
    370                 375                 380

Ser Ile Ile Pro Leu Arg Tyr Val His Glu Asn Thr Glu Leu Gly Gly
385                 390                 395                 400

Tyr His Val Pro Ser Gly Thr Glu Leu Ala Ile Asn Ile Tyr Gly Cys
                405                 410                 415

Asn Met Glu Arg Glu Ile Trp Glu Asp Pro Glu Glu Trp Asn Pro Glu
                420                 425                 430

Arg Phe Leu Ser Glu Lys Glu Pro Ile Asp Leu Gln Arg Thr Met Ala
            435                 440                 445

Phe Gly Gly Gly Lys Arg Val Cys Ala Gly Ala Met Gln Ala Met Leu
450                 455                 460

Ile Ala Cys Ala Ser Ile Gly Arg Met Val Arg Glu Phe Glu Trp Arg
465                 470                 475                 480

Leu Lys Asp Asp Thr Gly Glu Asp Val Asn Thr Leu Gly Leu Thr Thr
                485                 490                 495

Gln Lys Leu Asn Pro Met Leu Ala Val Ile Lys Pro Arg Asn
                500                 505                 510

<210> SEQ ID NO 18
<211> LENGTH: 1575
<212> TYPE: DNA
<213> ORGANISM: Stevia rebaudiana

<400> SEQUENCE: 18
```

| | | |
|---|---|---|
| atggtggctt tccctcaatt tctatcattt ttagggcttc tacttttgt tatatcctat | 60 |
| agttacaata taagaaaaag aagtaacaca aaaagaagta ttaaacctaa agctcctgaa | 120 |
| ccttcagggg cattgccttt tataggccac ctccattttc taagaagtca agttccttta | 180 |
| gcaaggatat ttggaaagat tgctgacgac tacgggccgg tttactcttt acggctcggt | 240 |
| tttcgtcaag cattggttgt aagcagttgg cagatggtca agaatgtttt caccacaaat | 300 |
| gacaaaaact tgcaaccag acccaacatg gcaattagcc ggcacatggt ctacaacaat | 360 |
| gctggttttg cactcgcgcc atatggacca tattggcgag agatccgaaa gattgttgct | 420 |
| tccgagcttt ttacatccca acgtgttgaa aagttcatga atgttcgtga ctcagaagtg | 480 |
| aaaaactcta ttaacgagct ctatttgttg tcctcaaaga aggcgaacgg atcatcgatt | 540 |
| gtggaaatga acaagtggtt tgaccacata acgttcaata taattataag aatcttagcg | 600 |
| gggaaaagat ttattaatgg ttgtaatgat gaaggtaata atgaagactc acatgtaaaa | 660 |
| caagccataa caagagggtt gtatgttagt ggtctttttg ttgtgtctga tttctttcca | 720 |
| tatcttgaat ggatggatat tgggggcat gtgaaagtta tgaaacatgt ggctaaagag | 780 |
| gttgatagtg ttgtgggaaa gtggcttgat gaacatattg agaagagaaa agaggcagag | 840 |

```
agtgacaaaa atgaagattt catggattta atgttgtcta cactgccaaa agatgctgaa    900
atgtctggtc atgggcgaga acagtcatc aaggcaacaa caatggtcct catgttgacg    960
ggttcagaaa gcactgcttt gacaatgaca tggacacttt ccttattact taaccatcct   1020
cgtgtactaa aagctgccca aaaagaactt gacatccatg ttggacaaaa gaaatgggtg   1080
gaagaatcag acatcacaaa tcttgtttat ctacaagcca tagtcaaaga aacactcaga   1140
atgtacccac cgggtccgtt ggccggacca catgaggcca ttgacgattg ctatatcggg   1200
ggctatcatg tcaccaaagg gactcgtttg attgtaaatg tttggaagct acatcgcgac   1260
ccacaagtct ggtcagatcc tcacgagttt cgaccagaga ggtttcttga ggagcactca   1320
gagataaatt atcagggtca gactttgaa tacattccat ttagcacggg aaggagaatg   1380
tgccccgcaa cctcgtttgc ttggcatgta attcatttga cacttgcgcg gttacttcaa   1440
gggtttgact tgtcaacacc catggggaag cctattgata tgagtgaggg cttaggaatt   1500
gcgttatcta aggtgaaacc agttgaagtt atcatcactc cacgtctttc tccagagctc   1560
tatgaaacga tttaa                                                    1575
```

```
<210> SEQ ID NO 19
<211> LENGTH: 524
<212> TYPE: PRT
<213> ORGANISM: Stevia rebaudiana

<400> SEQUENCE: 19
```

```
Met Val Ala Phe Pro Gln Phe Leu Ser Phe Leu Gly Leu Leu Leu Phe
  1               5                  10                  15

Val Ile Ser Tyr Ser Tyr Asn Ile Arg Lys Arg Ser Asn Thr Lys Arg
             20                  25                  30

Ser Ile Lys Pro Lys Ala Pro Glu Pro Ser Gly Ala Leu Pro Phe Ile
         35                  40                  45

Gly His Leu His Phe Leu Arg Ser Gln Val Pro Leu Ala Arg Ile Phe
     50                  55                  60

Gly Lys Ile Ala Asp Asp Tyr Gly Pro Val Tyr Ser Leu Arg Leu Gly
 65                  70                  75                  80

Phe Arg Gln Ala Leu Val Val Ser Ser Trp Gln Met Val Lys Glu Cys
                 85                  90                  95

Phe Thr Thr Asn Asp Lys Asn Phe Ala Thr Arg Pro Asn Met Ala Ile
            100                 105                 110

Ser Arg His Met Val Tyr Asn Asn Ala Gly Phe Ala Leu Ala Pro Tyr
        115                 120                 125

Gly Pro Tyr Trp Arg Glu Ile Arg Lys Ile Val Ala Ser Glu Leu Phe
    130                 135                 140

Thr Ser Gln Arg Val Glu Lys Phe Met Asn Val Arg Asp Ser Glu Val
145                 150                 155                 160

Lys Asn Ser Ile Asn Glu Leu Tyr Leu Leu Ser Lys Lys Ala Asn
                165                 170                 175

Gly Ser Ser Ile Val Glu Met Asn Lys Trp Phe Asp His Ile Thr Phe
            180                 185                 190

Asn Ile Ile Ile Arg Ile Leu Ala Gly Lys Arg Phe Ile Asn Gly Cys
        195                 200                 205

Asn Asp Glu Gly Asn Asn Glu Asp Ser His Val Lys Gln Ala Ile Thr
    210                 215                 220

Arg Gly Leu Tyr Val Ser Gly Leu Phe Val Val Ser Asp Phe Phe Pro
225                 230                 235                 240
```

```
Tyr Leu Glu Trp Met Asp Ile Gly Gly His Val Lys Val Met Lys His
                245                 250                 255
Val Ala Lys Glu Val Asp Ser Val Val Gly Lys Trp Leu Asp His
        260                 265                 270
Ile Glu Lys Arg Lys Glu Ala Glu Ser Asp Lys Asn Glu Asp Phe Met
            275                 280                 285
Asp Leu Met Leu Ser Thr Leu Pro Lys Asp Ala Glu Met Ser Gly His
        290                 295                 300
Gly Arg Glu Thr Val Ile Lys Ala Thr Thr Met Val Leu Met Leu Thr
305                 310                 315                 320
Gly Ser Glu Ser Thr Ala Leu Thr Met Thr Trp Thr Leu Ser Leu Leu
                325                 330                 335
Leu Asn His Pro Arg Val Leu Lys Ala Ala Gln Lys Glu Leu Asp Ile
            340                 345                 350
His Val Gly Gln Lys Lys Trp Val Glu Glu Ser Asp Ile Thr Asn Leu
        355                 360                 365
Val Tyr Leu Gln Ala Ile Val Lys Glu Thr Leu Arg Met Tyr Pro Pro
    370                 375                 380
Gly Pro Leu Ala Gly Pro His Glu Ala Ile Asp Asp Cys Tyr Ile Gly
385                 390                 395                 400
Gly Tyr His Val Thr Lys Gly Thr Arg Leu Ile Val Asn Val Trp Lys
                405                 410                 415
Leu His Arg Asp Pro Gln Val Trp Ser Asp Pro His Glu Phe Arg Pro
            420                 425                 430
Glu Arg Phe Leu Glu His Ser Glu Ile Asn Tyr Gln Gly Gln Asn
        435                 440                 445
Phe Glu Tyr Ile Pro Phe Ser Thr Gly Arg Arg Met Cys Pro Ala Thr
    450                 455                 460
Ser Phe Ala Trp His Val Ile His Leu Thr Leu Ala Arg Leu Leu Gln
465                 470                 475                 480
Gly Phe Asp Leu Ser Thr Pro Met Gly Lys Pro Ile Asp Met Ser Glu
                485                 490                 495
Gly Leu Gly Ile Ala Leu Ser Lys Val Lys Pro Val Gly Val Ile Ile
            500                 505                 510
Thr Pro Arg Leu Ser Pro Glu Leu Tyr Glu Thr Ile
        515                 520

<210> SEQ ID NO 20
<211> LENGTH: 1431
<212> TYPE: DNA
<213> ORGANISM: Stevia rebaudiana

<400> SEQUENCE: 20
atgattcaag ttctaacacc gatccttctc ttcctcattt tcttcgtttt ctggaaggtt      60
tacaagcacc agaaaaccaa aataaatctt ccaccgggaa gcttcggatg gccatttctg     120
ggcgaaactc tggcactcct acgtgcaggt tgggattcag agccggagag atttgttcgt     180
gaacggatca gaaacacgg aagtcctcta gtgtttaaga cgtcgttgtt tggcgaccgt     240
tttgcggtgt tgtgtggacc tgccggaaac aagttcctgt tctgcaacga gaacaagctg     300
gtagcgtcgt ggtggccagt tccggtgagg aagcttttcg gcaagtctct gctcacgatt     360
cgtggtgatg aagctaagtg gatgaggaag atgttgttat cgtatcttgg tcctgatgct     420
ttcgcaactc attatgccgt caccatggac gtcgtcaccc gtcggcatat cgacgttcat     480
tggcgaggga aggaagaggt gaacgtattc caaaccgtta agttatatgc ctttgagctt     540
```

-continued

```
gcatgtcgtt tattcatgaa cctagacgac ccaaaccaca ttgcaaaact cggttccttg    600
ttcaacattt tcttgaaagg catcattgag cttccaatcg acgtcccagg gacacgattt   660
tatagctcca aaaaagcagg agcagctatc aggattgaac taaaaaaatt gattaaagca    720
agaaaactgg aactgaaaga agggaaggca tcatcttcac aagacctctt atcacatttg    780
cttacatctc cagatgaaaa tggtatgttt ctaaccgaag aagagattgt agacaacatc    840
ttgttactac tctttgcggg tcatgatacc tcggctcttt caatcacttt gctcatgaag    900
actcttggcg aacattctga tgtttatgac aaggtgttaa aagagcaact agagatatcg    960
aagacgaaag aagcatggga gtccctgaaa tgggaggaca tacaaaagat gaaatactcc   1020
tggagtgttg tatgtgaagt catgagacta aatccacctg ttataggaac ctatagagag   1080
gcccttgtgg atattgatta tgcgggttat accatcccca aaggatggaa gctacactgg   1140
agtgctgtat cgacacaaag ggacgaggct aactttgaag acgtaacacg ttttgaccca   1200
tcacggtttg aaggcgcagg accgactcca ttcacctttg ttccgtttgg aggggggcct   1260
agaatgtgtt tagggaaaga atttgctcga ttggaagtac ttgcgtttct tcacaatatt   1320
gtcaccaatt tcaaatggga cctgttgata cctgatgaga aaatagaata tgatcccatg   1380
gctaccccag caagggggct tccaattcgt cttcatcccc atcaagtttg a             1431
```

<210> SEQ ID NO 21
<211> LENGTH: 476
<212> TYPE: PRT
<213> ORGANISM: Stevia rebaudiana

<400> SEQUENCE: 21

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
                20                  25                  30

Gly Ser Phe Gly Trp Pro Phe Leu Gly Glu Thr Leu Ala Leu Leu Arg
            35                  40                  45

Ala Gly Trp Asp Ser Glu Pro Glu Arg Phe Val Arg Glu Arg Ile Lys
        50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
                100                 105                 110

Phe Gly Lys Ser Leu Leu Thr Ile Arg Gly Asp Glu Ala Lys Trp Met
            115                 120                 125

Arg Lys Met Leu Leu Ser Tyr Leu Gly Pro Asp Ala Phe Ala Thr His
        130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
                180                 185                 190

His Ile Ala Lys Leu Gly Ser Leu Phe Asn Ile Phe Leu Lys Gly Ile
            195                 200                 205

Ile Glu Leu Pro Ile Asp Val Pro Gly Thr Arg Phe Tyr Ser Ser Lys
        210                 215                 220
```

-continued

```
Lys Ala Gly Ala Ala Ile Arg Ile Glu Leu Lys Lys Leu Ile Lys Ala
225                 230                 235                 240

Arg Lys Leu Glu Leu Lys Glu Gly Lys Ala Ser Ser Gln Asp Leu
            245                 250                 255

Leu Ser His Leu Leu Thr Ser Pro Asp Glu Asn Gly Met Phe Leu Thr
        260                 265                 270

Glu Glu Glu Ile Val Asp Asn Ile Leu Leu Leu Phe Ala Gly His
            275                 280                 285

Asp Thr Ser Ala Leu Ser Ile Thr Leu Leu Met Lys Thr Leu Gly Glu
        290                 295                 300

His Ser Asp Val Tyr Asp Lys Val Leu Lys Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Val Cys Glu Val Met Arg Leu Asn Pro
            340                 345                 350

Pro Val Ile Gly Thr Tyr Arg Glu Ala Leu Val Asp Ile Asp Tyr Ala
        355                 360                 365

Gly Tyr Thr Ile Pro Lys Gly Trp Lys Leu His Trp Ser Ala Val Ser
    370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
                405                 410                 415

Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
        435                 440                 445

Leu Ile Pro Asp Glu Lys Ile Glu Tyr Asp Pro Met Ala Thr Pro Ala
    450                 455                 460

Lys Gly Leu Pro Ile Arg Leu His Pro His Gln Val
465                 470                 475
```

<210> SEQ ID NO 22
<211> LENGTH: 1569
<212> TYPE: DNA
<213> ORGANISM: Stevia rebaudiana

<400> SEQUENCE: 22

```
atgggtctct tccctttgga agatagttac gcactcgtct ttgaaggttt agcaataact      60
ctagctctct actacttatt atccttcatc tataaaacct ctaaaaagac ttgtactcca     120
cctaaagcaa gcggtgagca ccctataaca ggccacttaa accttcttag tggttcatcc     180
ggtcttcccc atctagcctt agcatctttg ctgaccgat gtgggcccat attccatc       240
cgacttggca tacgtagagt tttggtggtt agtaattggg aaattgctaa ggagatcttc     300
actacccatg atttgattgt ttcaaaccgt cccaaatacc tcgctgcaaa gattttggga     360
ttcaactatg tgtccttttc gtttgctcca tatggcccct attgggttgg aatccgtaag     420
atcatcgcca caaaactgat gtcaagtagc aggctccaga agcttcagtt tgtccgagtt     480
ttcgaactag aaaactccat gaaaagcata cgcgagtctt ggaaagagaa aaaagacgaa     540
gaaggtaaag tgttggtgga gatgaaaaaa tggttttggg aattgaatat gaatatagtt     600
cttagaactg ttgctggtaa acagtacact ggaactgttg atgatgcgga tcgaagagg      660
attagtgaat tgtttagaga atggtttcat tacacaggaa ggtttgttgt gggagatgct     720
```

-continued

```
tttcctttc ttgggtggtt ggatttgggt ggatataaga agaccatgga actagtggct      780
tccagactag attccatggt ctcaaaatgg ttagacgagc atcgcaaaaa gcaggctaac      840
gacgacaaaa aagaggacat ggatttcatg gacatcatga tatcgatgac tgaagccaat      900
tccccttttgg agggttatgg tacggataca ataattaaaa ccacttgcat gactcttatt      960
gtcagtggtg tagatacaac ctccatcgtg ctaacttggg cactctcgtt actactgaac     1020
aaccgtgaca ctcttaagaa agctcaagaa gagctagaca tgtgtgtggg aaaaggtcga     1080
caagtaaacg aatcagatct agtaaaccta atctaccttg aagccgtatt aaaagaagca     1140
ttgcgactat acccagcagc attccttgga ggtcctagag ccttttttaga agactgcacc    1200
gtggcagggt accgtatccc aaaaggcaca tgtctactta ttaacatgtg gaaacttcat     1260
cgtgatccaa acatatggtc agacccatgt gagtttaaac cagagaggtt cttaaccca     1320
aaccaaaagg acgtagatgt tattggaatg gattttgagt taatcccatt tggtgcggga     1380
agaaggtatt gtccagggac acgtttggca ttacaaatgt tacacatagt tctggccact     1440
ctactacaaa actttgagat gtcaactcca aatgatgcac ccgttgatat gaccgcgagt     1500
gttggaatga caaatgcgaa ggcaagtcca cttgaagttc tactttcgcc acgtgttaag     1560
tggtcatag                                                             1569
```

<210> SEQ ID NO 23
<211> LENGTH: 522
<212> TYPE: PRT
<213> ORGANISM: Stevia rebaudiana

<400> SEQUENCE: 23

```
Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Leu Ser Phe Ile Tyr Lys
            20                  25                  30

Thr Ser Lys Lys Thr Cys Thr Pro Pro Lys Ala Ser Gly Glu His Pro
        35                  40                  45

Ile Thr Gly His Leu Asn Leu Leu Ser Gly Ser Ser Gly Leu Pro His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
            100                 105                 110

Tyr Leu Ala Ala Lys Ile Leu Gly Phe Asn Tyr Val Ser Phe Ser Phe
        115                 120                 125

Ala Pro Tyr Gly Pro Tyr Trp Val Gly Ile Arg Lys Ile Ile Ala Thr
    130                 135                 140

Lys Leu Met Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190

Trp Glu Leu Asn Met Asn Ile Val Leu Arg Thr Val Ala Gly Lys Gln
        195                 200                 205

Tyr Thr Gly Thr Val Asp Asp Ala Asp Ala Lys Arg Ile Ser Glu Leu
    210                 215                 220
```

```
Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
            245                 250                 255

Glu Leu Val Ala Ser Arg Leu Asp Ser Met Val Ser Lys Trp Leu Asp
        260                 265                 270

Glu His Arg Lys Lys Gln Ala Asn Asp Asp Lys Lys Glu Asp Met Asp
    275                 280                 285

Phe Met Asp Ile Met Ile Ser Met Thr Glu Ala Asn Ser Pro Leu Glu
290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
            325                 330                 335

Leu Leu Leu Asn Asn Arg Asp Thr Leu Lys Lys Ala Gln Glu Glu Leu
        340                 345                 350

Asp Met Cys Val Gly Lys Gly Arg Gln Val Asn Glu Ser Asp Leu Val
    355                 360                 365

Asn Leu Ile Tyr Leu Glu Ala Val Leu Lys Glu Ala Leu Arg Leu Tyr
370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
            405                 410                 415

Trp Lys Leu His Arg Asp Pro Asn Ile Trp Ser Asp Pro Cys Glu Phe
        420                 425                 430

Lys Pro Glu Arg Phe Leu Thr Pro Asn Gln Lys Asp Val Asp Val Ile
    435                 440                 445

Gly Met Asp Phe Glu Leu Ile Pro Phe Gly Ala Gly Arg Arg Tyr Cys
450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
            485                 490                 495

Met Thr Ala Ser Val Gly Met Thr Asn Ala Lys Ala Ser Pro Leu Glu
        500                 505                 510

Val Leu Leu Ser Pro Arg Val Lys Trp Ser
    515                 520

<210> SEQ ID NO 24
<211> LENGTH: 1440
<212> TYPE: DNA
<213> ORGANISM: Stevia rebaudiana

<400> SEQUENCE: 24
atgattcaag ttctaacacc gatcatcctc ttcatcatta tctacgtttt ctggaacgtt      60
tataagaacc agaaatcggg aagaaacaaa atcaaacttc accgggaag cttcggatgg     120 ccgtttgtgg gcgaaactct cgccatgcta cgtgcaaatt gggacggagt gccggaaga     180 ttcgtcaaag aacggatcga gaaacacgga accctcaag tgtttaaaac gtcgttgttt     240
ggcgaccgta tggcggtgtt gtgtggacct gctggaaaca gtttctgtt tggtaacgag     300 aacaagctgg tggcggtgtg gtggccgttg ccggtgagga agcttttcgg caagtgtctg     360 attcaaccc gtggggatga agctaagtgg atgaggaaga tgctgttatc gtatcttggt     420
cctgatgctt tcgcaattca ttatgccgtc accatggata tcgtcacccg tcggcatatc     480
```

-continued

```
gacgttcatt ggcgaggcaa gaaagaggtg aatgtgttcc aaactattaa gttatatgcc      540
tttgagcttg catgcagttt attcatgagc ttggaggacc caaatcacat tgcaaaactt      600
gcttccttgt ttaacatttt cttgaaaggc gtgattgagc ttccaatcaa cgtcccgggg      660
acacgatttt atagctccaa caaagcggga gcatctattc ggaccgaact acaaacaatt      720
atcaaagcaa gaaacaagaa actgaaagaa ggaaaggcat catattcaca agacctctta      780
tcacatttgc ttacatcttc agatgaaaat ggcaagtatc taaacgagaa agagattgcg      840
aataacatct tattattact atttgcgggt catgacacct cggctgtttc tatcacttta      900
ctcatgaaga ctcttggcga acattctgat gtctatgaca aggtgttaaa agagcaatta      960
gagatctcta aggggaaaga agcagggaaa ttgctgaaat gggaggacat acggaagatg     1020
aaatactctt ggagtgttgt atctgaagtc atgagactaa atccacctgt taccggagcc     1080
tatagagaag ctctagtgga tatcgagtat ggaggttata ccatcccaa aggatggaag     1140 atacaatgga gtgctgcatc aacacaaagg gacgaggcta actttaaaga cgtgactcgt     1200
tttgacccat cacggtttga aggcgtggga ccgactccat tcacatatgt tccatttgga     1260
gggggtccta aatgtgtttt aggaaaagaa tttgctcgat ggaagtgct tgcattcctt     1320 cacaacattg tcatcaactt taaatgggac ctactaattc cagatgagaa aatagaatat     1380
gatcctatgg ctaccccagt aaaagggctt ccaattcgtc tttatcctca tcaagtttga     1440
```

<210> SEQ ID NO 25
<211> LENGTH: 479
<212> TYPE: PRT
<213> ORGANISM: Stevia rebaudiana

<400> SEQUENCE: 25

```
Met Ile Gln Val Leu Thr Pro Ile Ile Leu Phe Ile Ile Tyr Val
1               5                   10                  15

Phe Trp Asn Val Tyr Lys Asn Gln Lys Ser Gly Arg Asn Lys Ile Lys
            20                  25                  30

Leu Pro Pro Gly Ser Phe Gly Trp Pro Phe Val Gly Glu Thr Leu Ala
        35                  40                  45

Met Leu Arg Ala Asn Trp Asp Gly Val Pro Glu Arg Phe Val Lys Glu
    50                  55                  60

Arg Ile Glu Lys His Gly Asn Pro Gln Val Phe Lys Thr Ser Leu Phe
65                  70                  75                  80

Gly Asp Arg Met Ala Val Leu Cys Gly Pro Ala Gly Asn Lys Phe Leu
                85                  90                  95

Phe Gly Asn Glu Asn Lys Leu Val Ala Val Trp Trp Pro Leu Pro Val
            100                 105                 110

Arg Lys Leu Phe Gly Lys Cys Leu Ile Thr Thr Arg Gly Asp Glu Ala
        115                 120                 125

Lys Trp Met Arg Lys Met Leu Leu Ser Tyr Leu Gly Pro Asp Ala Phe
    130                 135                 140

Ala Ile His Tyr Ala Val Thr Met Asp Ile Val Thr Arg Arg His Ile
145                 150                 155                 160

Asp Val His Trp Arg Gly Lys Lys Glu Val Asn Val Phe Gln Thr Ile
                165                 170                 175

Lys Leu Tyr Ala Phe Glu Leu Ala Cys Ser Leu Phe Met Ser Leu Glu
            180                 185                 190

Asp Pro Asn His Ile Ala Lys Leu Ala Ser Leu Phe Asn Ile Phe Leu
        195                 200                 205
```

```
Lys Gly Val Ile Glu Leu Pro Ile Asn Val Pro Gly Thr Arg Phe Tyr
        210                 215                 220

Ser Ser Asn Lys Ala Gly Ala Ser Ile Arg Thr Glu Leu Gln Thr Ile
225                 230                 235                 240

Ile Lys Ala Arg Lys Gln Glu Leu Lys Glu Gly Lys Ala Ser Tyr Ser
                245                 250                 255

Gln Asp Leu Leu Ser His Leu Leu Thr Ser Ser Asp Glu Asn Gly Lys
            260                 265                 270

Tyr Leu Asn Glu Lys Glu Ile Ala Asn Asn Ile Leu Leu Leu Leu Phe
        275                 280                 285

Ala Gly His Asp Thr Ser Ala Val Ser Ile Thr Leu Leu Met Lys Thr
    290                 295                 300

Leu Gly Glu His Ser Asp Val Tyr Asp Lys Val Leu Lys Glu Gln Leu
305                 310                 315                 320

Glu Ile Ser Lys Gly Lys Glu Ala Gly Glu Leu Leu Lys Trp Glu Asp
                325                 330                 335

Ile Arg Lys Met Lys Tyr Ser Trp Ser Val Val Ser Glu Val Met Arg
            340                 345                 350

Leu Asn Pro Pro Val Thr Gly Ala Tyr Arg Glu Ala Leu Val Asp Ile
        355                 360                 365

Glu Tyr Gly Gly Tyr Thr Ile Pro Lys Gly Trp Lys Ile Gln Trp Ser
    370                 375                 380

Ala Ala Ser Thr Gln Arg Asp Glu Ala Asn Phe Lys Asp Val Thr Arg
385                 390                 395                 400

Phe Asp Pro Ser Arg Phe Glu Gly Val Gly Pro Thr Pro Phe Thr Tyr
                405                 410                 415

Val Pro Phe Gly Gly Gly Pro Arg Met Cys Leu Gly Lys Glu Phe Ala
            420                 425                 430

Arg Leu Glu Val Leu Ala Phe Leu His Asn Ile Val Ile Asn Phe Lys
        435                 440                 445

Trp Asp Leu Leu Ile Pro Asp Glu Lys Ile Glu Tyr Asp Pro Met Ala
    450                 455                 460

Thr Pro Val Lys Gly Leu Pro Ile Arg Leu Tyr Pro His Gln Val
465                 470                 475

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cacggatccc ccttatgaaa ttcaaaaagt t                              31

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caacatggat cttaaattac                                           20

<210> SEQ ID NO 28
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctggatccaa tgattcaagt tctaacaccg atc                                    33

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgactcact atagggcgaa ttgg                                              24

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
catgaattcg ataacgacag agcgatgga                                         29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caagaattcc gaggtcataa gctagtgta                                         29

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caggatccaa acaaagaatg attc                                              24

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gattcagtta cttacaggca caa                                               23

<210> SEQ ID NO 34
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 34
catggatcca taattatggg tctcttcc                                          28

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caagaattct caataacctt aataaccat                                         29

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggctctaact cacgatattg                                                   20

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37 agtggtctctt gtcctgca                                                    19

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttgcgatgaa agctggagaa                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
taatacgact cactataggg                                                   20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                                    -continued
    primer

<400> SEQUENCE: 40
tatttaggtg acactataga at                                              22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tctaaccgac ttcatgatct                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccctccaagc tctgtgtttt                                                 20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccggcacatg gtctacaac                                                  19

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agccctcact catatcaata g                                               21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gaggcagaga gtgacaaaaa                                                 20

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 46
ccataaacca ttatatcata tatt                                            24

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccgcgcaagt gtcaaatgaa                                                 20

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cctcactaaa gggaacaaaa gctg                                            24

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggcatcattg agcttccaat                                                 20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgtgttaccg tcttcaaagt t                                               21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtcacggttg ttcagtagta a                                               21

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
```

-continued gacgaagaag gtaaag                                                            16

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggccatatgg agcaaac                                                           17

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agtaaaccta atctaccttg aa                                                     22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gccgtcacca tggatatcgt                                                        20

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttactatttg cgggtcatga c                                                      21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caggtggatt tagtctcatg a                                                      21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cccagtcacg acgttgtaaa acg                                                    23

```
<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 tttaacaccct tgtcatagac                                              20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: n is a modified or unusual nucleotide

<400> SEQUENCE: 60
nagagcaatt agagatctct a                                             21

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gctgatggcg atgaatgaac actg                                          24

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgcggatccg aacactgcgt ttgctggctt tgatg                              35

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccataagttt ctgcccattt t                                             21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
```

-continued

```
ttggcaatcc tggtacctca                                              20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cgtgttaccg tcttcaaagt t                                            21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggttcctata acaggtggat t                                            21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atctttgcag cgaggtattt g                                            21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aacacattca cctctttctt g                                            21
```